(12) United States Patent
Mueller et al.

(10) Patent No.: US 8,729,299 B2
(45) Date of Patent: May 20, 2014

(54) PROCESSES FOR THE PRODUCTION OF ACRYLIC ACIDS AND ACRYLATES

(75) Inventors: Sean Mueller, Pasadena, TX (US);
Josefina Chapman, Houston, TX (US);
Craig Peterson, Houston, TX (US);
Dick Nagaki, The Woodlands, TX (US)

(73) Assignee: Celanese International Corporation, Dallas, TX (US)

( * ) Notice: Subject to any disclaimer, the term of this patent is extended or adjusted under 35 U.S.C. 154(b) by 40 days.

(21) Appl. No.: 13/428,065

(22) Filed: Mar. 23, 2012

(65) Prior Publication Data

US 2013/0085296 A1   Apr. 4, 2013

Related U.S. Application Data

(63) Continuation-in-part of application No. 13/251,623, filed on Oct. 3, 2011, now Pat. No. 8,658,823.

(51) Int. Cl.
*C07C 57/02* (2006.01)

(52) U.S. Cl.
USPC ........................................................ 562/598

(58) Field of Classification Search
CPC .................................................. C07C 51/353
See application file for complete search history.

(56) References Cited

U.S. PATENT DOCUMENTS

| | | | |
|---|---|---|---|
| 3,541,143 A | 11/1970 | Nakano et al. | |
| 4,677,225 A * | 6/1987 | Niizuma et al. | 562/599 |
| 4,994,608 A | 2/1991 | Torrence et al. | |
| 5,001,259 A | 3/1991 | Smith et al. | |
| 5,026,908 A | 6/1991 | Smith et al. | |
| 5,144,068 A | 9/1992 | Smith et al. | |
| 5,364,824 A | 11/1994 | Andrews et al. | |
| 5,504,247 A | 4/1996 | Saxer et al. | |
| 5,523,480 A | 6/1996 | Bauer, Jr. et al. | |
| RE35,377 E | 11/1996 | Steinberg et al. | |
| 5,599,976 A | 2/1997 | Scates et al. | |
| 5,821,111 A | 10/1998 | Gaddy et al. | |
| 6,143,930 A | 11/2000 | Singh et al. | |
| 6,232,352 B1 | 5/2001 | Vidalin et al. | |
| 6,627,770 B1 | 9/2003 | Cheung et al. | |
| 6,657,078 B2 | 12/2003 | Scates et al. | |
| 6,685,754 B2 | 2/2004 | Kindig et al. | |
| 6,852,881 B2 | 2/2005 | De Decker et al. | |
| 7,005,541 B2 | 2/2006 | Cheung et al. | |
| 7,115,772 B2 | 10/2006 | Picard et al. | |
| 7,208,624 B2 | 4/2007 | Scates et al. | |
| 7,300,555 B2 | 11/2007 | Schroeder | |
| 7,803,969 B2 | 9/2010 | Nordhoff et al. | |
| 7,842,844 B2 | 11/2010 | Atkins | |
| 8,299,132 B2 | 10/2012 | Gracey et al. | |
| 8,299,133 B2 | 10/2012 | Gracey et al. | |
| 8,329,960 B2 | 12/2012 | Gracey et al. | |
| 8,378,153 B2 | 2/2013 | Daniel et al. | |

| | | |
|---|---|---|
| 2009/0048354 A1 | 2/2009 | Bell et al. |
| 2012/0071687 A1 | 3/2012 | Herzog et al. |
| 2012/0071688 A1 | 3/2012 | Herzog et al. |

FOREIGN PATENT DOCUMENTS

| | | |
|---|---|---|
| EP | 0124380 A1 * | 11/1984 |
| EP | 1741692 | 1/2007 |
| EP | 1904426 | 4/2008 |
| EP | 1907344 | 4/2008 |
| EP | 1914219 | 4/2008 |
| EP | 1923380 | 5/2008 |
| EP | 1967507 | 9/2008 |
| EP | 2060553 | 5/2009 |
| EP | 2060555 | 5/2009 |
| EP | 2070486 | 6/2009 |
| EP | 2072487 | 6/2009 |
| EP | 2072488 | 6/2009 |
| EP | 2072490 | 6/2009 |
| EP | 2072492 | 6/2009 |
| EP | 2076480 | 7/2009 |
| EP | 2186787 | 5/2010 |
| WO | WO 99/52628 | 10/1999 |
| WO | WO 2007/003909 | 1/2007 |
| WO | WO 2009/141641 | 11/2009 |

OTHER PUBLICATIONS

International Search Report and Written Opinion mailed Feb. 1, 2013 in corresponding International Application No. PCT/US2012/058431.
Mamoru Al et al., "Production of methacrylic acid by vapor-phase aldol condensation of propionic acid with formaldehyde over silica-supported metal phosphate catalysts", Applied catalysis A: general, vol. 252, 2003, XP 002689805, p. 185-191.
Bosman, et al., Journal of Catalysis, vol. 148, p. 660 (1994).
Brinker C J & Scherer G W, "Sol-Gel Science" published by Academic Press (1990).
Iler R K, The Chemistry of Silica, (Wiley, New York, 1979).
Jubb & Bowen, Journal of Material Science, vol. 22, pp. 1963-1970 (1987).
M. Ai, Applied Catalysis, 36, pp. 221-230 (1988).
M. Ai, Applied Catalysis, 48, pp. 51-61 (1989).
M. Ai, Applied Catalysis, 221, 1989, p. 29-36.
M. Ai, Journal of Catalysis, 107, 1987, pp. 201-208.
M. Ai, Journal of Catalysis, 113, pp. 562-566 (1988).
M. Ai, Journal of Catalysis, 124, 1990, pp. 293-296.
M. Ai, Shokubai, 29, 522 (1987), www.shokubai.org/jnl/cgi-bin/ccotw.cgi.
Monros, et al., Journal of Material Science, vol. 28, p. 5832 (1993).

* cited by examiner

*Primary Examiner* — Paul A Zucker (57) ABSTRACT

In one embodiment, the invention is to a process for producing an acrylate product. The process comprises the step of reacting a reaction mixture comprising an alkanoic acid, an alkylenating agent, and oxygen over a catalyst and under conditions effective to form a crude acrylate product. Preferably, the reaction mixture comprises from 0.5 wt % to 10 wt % oxygen. The crude acrylate product comprises acrylate product and alkylenating agent. The process further comprises the step of separating at least a portion of the crude product to form at least one alkylenating agent stream and at least one purified acrylate product stream. The purified acrylate product stream comprises acrylate product.

15 Claims, 5 Drawing Sheets

PROCESSES FOR THE PRODUCTION OF ACRYLIC ACIDS AND ACRYLATES

CROSS REFERENCE TO RELATED APPLICATIONS

This application claims priority to U.S. patent application Ser. No. 13/251,623, which was filed on Oct. 3, 2011. The entirety of this application is incorporated by reference herein.

FIELD OF THE INVENTION

The present invention relates generally to the production of acrylic acid via the condensation reaction of an alkanoic acid and an alkylenating agent, and oxygen. More specifically, the present invention relates to use of specific concentrations of oxygen in the condensation reaction mixture.

BACKGROUND OF THE INVENTION $\alpha,\beta$-unsaturated acids, particularly acrylic acid and methacrylic acid, and the ester derivatives thereof are useful organic compounds in the chemical industry. These acids and esters are known to readily polymerize or co-polymerize to form homopolymers or copolymers. Often the polymerized acids are useful in applications such as superabsorbents, dispersants, flocculants, and thickeners. The polymerized ester derivatives are used in coatings (including latex paints), textiles, adhesives, plastics, fibers, and synthetic resins.

Because acrylic acid and its esters have long been valued commercially, many methods of production have been developed. One exemplary acrylic acid ester production process utilizes: (1) the reaction of acetylene with water and carbon monoxide; and/or (2) the reaction of an alcohol and carbon monoxide, in the presence of an acid, e.g., hydrochloric acid, and nickel tetracarbonyl, to yield a crude product comprising the acrylate ester as well as hydrogen and nickel chloride. Another conventional process involves the reaction of ketene (often obtained by the pyrolysis of acetone or acetic acid) with formaldehyde, which yields a crude product comprising acrylic acid and either water (when acetic acid is used as a pyrolysis reactant) or methane (when acetone is used as a pyrolysis reactant). These processes have become obsolete for economic, environmental, or other reasons.

More recent acrylic acid production processes have relied on the gas phase oxidation of propylene, via acrolein, to form acrylic acid. The reaction can be carried out in single- or two-step processes but the latter is favored because of higher yields. The oxidation of propylene produces acrolein, acrylic acid, acetaldehyde and carbon oxides. Acrylic acid from the primary oxidation can be recovered while the acrolein is fed to a second step to yield the crude acrylic acid product, which comprises acrylic acid, water, small amounts of acetic acid, as well as impurities such as furfural, acrolein, and propionic acid. Purification of the crude product may be carried out by azeotropic distillation. Although this process may show some improvement over earlier processes, this process suffers from production and/or separation inefficiencies. In addition, this oxidation reaction is highly exothermic and, as such, creates an explosion risk. As a result, more expensive reactor design and metallurgy are required. Also, the cost of propylene is often prohibitive.

The aldol condensation reaction of formaldehyde and acetic acid and/or carboxylic acid esters has been disclosed in literature. This reaction forms acrylic acid and is often conducted over a catalyst. For example, condensation catalysts consisting of mixed oxides of vanadium and phosphorus were investigated and described in M. Ai, *J. Catal.*, 107, 201 (1987); M. Ai, *J. Catal.*, 124, 293 (1990); M. Ai, *Appl. Catal.*, 36, 221 (1988); and M. Ai, *Shokubai*, 29, 522 (1987). The acetic acid conversions in these reactions, however, may leave room for improvement. Although this reaction is disclosed, there has been little if any disclosure relating to: 1) the effects of reactant feed parameters on the aldol condensation crude product; or 2) separation schemes that may be employed to effectively provide purified acrylic acid from the aldol condensation crude product.

Thus, the need exists for a process for producing purified acrylic acid, which provides improvements in yield, catalyst performance, and/or separation efficiencies.

The references mentioned above are hereby incorporated by reference.

BRIEF DESCRIPTION OF DRAWINGS

The invention is described in detail below with reference to the appended drawings, wherein like numerals designate similar parts.

SUMMARY OF THE INVENTION

In one embodiment, the invention relates to a process for producing an acrylate product. The process comprises the step of reacting a reaction mixture comprising an alkanoic acid, an alkylenating agent, and oxygen over a catalyst and under conditions effective to form a crude acrylate product. Preferably, the reaction mixture comprises from 0.5 wt % to 10 wt % oxygen. The crude acrylate product comprises acrylate product and alkylenating agent. The process further comprises the step of separating at least a portion of the crude product to form at least one alkylenating agent stream and at least one purified acrylate product stream. The purified acrylate product stream comprises acrylate product. Preferably, reaction yield varies by less than 50% over a lifetime of the catalyst.

In another embodiment, the process comprises the step of determining a reaction selectivity to carbon monoxide and/or carbon dioxide. The process further comprises the step of adjusting the oxygen concentration in the reaction mixture based on the selectivity to carbon monoxide and/or carbon dioxide.

DETAILED DESCRIPTION OF THE INVENTION

Introduction

Production of unsaturated carboxylic acids such as acrylic acid and methacrylic acid and the ester derivatives thereof via most conventional processes have been limited by economic and environmental constraints. In the interest of finding a new reaction path, the aldol condensation reaction of acetic acid and an alkylenating agent, e.g., formaldehyde, has been investigated. This reaction may yield a unique crude product that comprises, inter alia, a higher amount of (residual) formaldehyde, which is generally known to add unpredictability and problems to separation schemes. Although the aldol condensation reaction of acetic acid and formaldehyde is known, there has been little if any disclosure relating to the effects of reactant feed parameters on the aldol condensation crude product.

It has now been discovered that the amount of oxygen that is fed to the aldol condensation reaction may significantly affect, inter alia, catalyst stability as well as overall reaction yield. As one example, in cases where little or no oxygen is utilized in the reaction mixture, the catalyst stability reduces very quickly, e.g., the reaction yield decreases significantly over a short time period. It has now been discovered, surprisingly, that when the oxygen content of the reaction mixture is increased to a certain level however, the drop off in catalyst stability over time, surprisingly, is reduced, e.g. the yield achieved by the catalyst increases and/or becomes more consistent over time. These unexpected improvements in yield and stability increase as oxygen concentration is increased, at least to a certain point. Reaction yield may be defined in terms of moles of a particular reactant. For example, reaction yield may be defined as the number of moles of acrylate product, e.g., acrylic acid, that is formed compared to the number of moles of reactant, e.g., acetic acid, that is fed to the reactor. It has further been found that, as the oxygen content in the reaction mixture continues to increase, yields unexpectedly begin to again decrease. Without being bound by theory, it is believed that as oxygen levels increase past a certain level, e.g., 10 wt %, selectivity toward by-products, e.g., carbon monoxide and carbon dioxide, increases. As a result, less acrylic acid is produced and yield decreases. Surprisingly, when the amount of oxygen in the reaction mixture is maintained at specific levels, e.g., within specific ranges, 1) catalyst stability over time is significantly improved, e.g., catalyst decay is reduced; and 2) overall reaction yield is improved, as compared to a similar process employing oxygen concentrations outside of the inventive range.

In one embodiment, the present invention relates to a process for producing acrylic acid, methacrylic acid, and/or the salts and esters thereof. As used herein, acrylic acid, methacrylic acid, and/or the salts and esters thereof, collectively or individually, may be referred to as "acrylate product" or "acrylate products." The use of the terms acrylic acid, methacrylic acid, or the salts and esters thereof, individually, does not exclude the other acrylate products, and the use of the term acrylate product does not require the presence of acrylic acid, methacrylic acid, and the salts and esters thereof.

The process comprises the step of reacting a reaction mixture comprising an alkanoic acid, an alkylenating agent, and oxygen over a catalyst and under conditions effective to form a crude acrylate product. Preferably, the reaction mixture comprises from 0.5 wt % to 10 wt % oxygen, e.g., from 0.5 wt % to 6 wt %, from 0.5 wt % to 5 wt %, from 0.5 wt % to 4 wt %, from 1 wt % to 3 wt %, or from 1 wt % to 2 wt %. These weight percentages may be based on the total weight of the reaction mixture. The amount of oxygen in the reaction mixture may also be characterized in terms of molar ratios. In one embodiment, a molar ratio of acetic acid to oxygen in the reaction mixture ranges from 2:1 to 30:1, e.g., from 5:1 to 25:1. In one embodiment, a molar ratio of acetic acid and alkylenating agent, combined, to oxygen in the reaction mixture ranges from 3:1 to 60:1, e.g., from 10:1 to 50:1.

By employing the inventive oxygen ranges, catalyst stability over time is beneficially improved. For example, catalyst stability may vary by less than 50%, e.g., less than 25% or less than 10%, over a predetermined period of time, e.g., a lifetime of the catalyst. In one embodiment, the predetermined period of time is at least 1 hour, e.g., at least 5 hours, at least 10 hours, at least 25 hours, or at least 50 hours. In terms of ranges the predetermined period of time may range from 1 hour to 100 hours, e.g., from 1 hour to 50 hours, or from 1 hour to 10 hours. It is also within the contemplation of the invention for the catalyst to demonstrate improved stability for greater than 100 hours and/or less than 1 hour. In conventional processes wherein oxygen concentration is maintained at levels outside the inventive levels, catalyst performance may show a significant decrease over time, e.g., greater than 50% after 5 hours. Catalyst stability may, in some embodiments, be characterized in terms of variance of conversion, selectivity, and/or yield. For example, the acetic acid conversion achieved when using the catalyst may vary by less than 50% over the lifetime of the catalyst.

In addition to the improvement in stability, the overall catalyst performance is also improved by employing the inventive oxygen concentration ranges. Catalyst performance may, in some embodiments, be determined based on overall yield of the reaction, which may be based on acetic acid fed to the reaction. Preferably, reaction yield is greater than 20%, e.g., greater than 25%, greater than 30%, greater than 35%, greater than 40%, or greater than 50%. In terms of ranges, reaction yield may range from 20% to 99%, e.g., from 20% to 75% or from 25% to 50%. In one embodiment, reaction yield is consistent over a predetermined period of time. For example yield may decrease (or increase) by less than 5% after the predetermined time, e.g., less than 4%, less than 3%, or less than 1%. In one embodiment, the overall reaction yield achieved by utilizing the inventive oxygen concentration ranges is at least 3% greater than yields achieved using oxygen concentrations outside of the inventive range, e.g., at least 5% greater than, at least 7% greater than, or at least 10% greater than.

In addition to oxygen, the reaction mixture may further comprise an alkanoic acid, e.g., acetic acid, and an alkylenating agent, e.g., formaldehyde. In one embodiment, the reaction mixture comprises from 1 wt % to 40% alkanoic acid, e.g., from 1 wt % to 30 wt % or from 5 wt % to 20 wt %; and from 0.5 wt % to 35 wt % alkylenating agent, e.g., from 0.5 wt % to 25 wt % or from 1 wt % to 15 wt %.

Water may also be present in the reactor. For example, the reaction mixture may comprise from 1 wt % to 60 wt % water, e.g., from 1 wt % to 40 wt % or from 5 wt % to 20 wt %. At least a portion of the water, however, is preferably removed prior to the condensation reaction for the reasons discussed above.

In one embodiment, a non-reactive gas e.g., an inert gas, is supplied to the reactor. Examples of non-reactive gases include, but are not limited to, nitrogen, helium, argon, and methane. For example, the reaction mixture may comprise from 25 wt % to 97.5 wt % inert gas, e.g., from 33 wt % to 90 wt %, from 40 wt % to 90 wt % or from 65 wt % to 85 wt %. Preferably, the inert gas is nitrogen. In a preferred embodiment, higher amounts of nitrogen are employed to dilute the reaction mixture, e.g., nitrogen dilution conditions. For example, the reaction mixture may comprise at least 74 wt % nitrogen, e.g., at least 80 wt %, at least 85 wt %, or at least 90 wt %.

In one embodiment, a reactive gas (other than the reactant gases) is supplied to the reactant stream. Examples of reactive gases or vapors include, but are not limited to, carbon oxides, sulfur oxides, and alkyl halides. When reactive gases are added to the reactor, these gases, in some embodiments, may be added in stages throughout the catalyst bed at desired levels as well as feeding with the other feed components at the beginning of the reactors. The addition of these additional components may improve reaction efficiencies.

Preferred embodiments of the inventive process demonstrate a low selectivity to undesirable products, such as carbon monoxide and carbon dioxide. The selectivity to these undesirable products preferably is less than 29%, e.g., less than 25%, less than 20%, less than 15%, or less than 10%. More preferably, these undesirable products are not detectable.

In one embodiment, the inventive process is controlled based on the carbon monoxide and/or carbon dioxide selectivity, which is decreased when the inventive oxygen amounts are utilized. As this selectivity exceeds a particular limit, the oxygen content of the reaction mixture is adjusted accordingly. In some embodiments, the process comprises the step of reacting the reaction mixture as discussed herein. The process may further comprise the step of determining the reaction selectivity to carbon monoxide and/or carbon dioxide. In some embodiments an acetic acid conversion is determined. The process further comprises the step of adjusting the oxygen concentration in the reaction mixture based on the selectivity determination. In these cases, as selectivity to carbon monoxide and/or carbon dioxide exceeds a predetermined level, the amount of oxygen fed to the reaction may be increased or decreased accordingly, e.g., the oxygen concentration is adjusted to be within the ranges discussed herein. In one embodiment, the oxygen concentration in the reaction mixture is reduced when the selectivity to carbon monoxide and/or carbon dioxide is greater than 29%.

Crude Acrylate Product

The aldol condensation reaction of the present invention, unlike most conventional acrylic acid-containing crude products, yields a crude acrylate product comprising acrylate product and a significant portion of at least one alkylenating agent. Preferably, the at least one alkylenating agent is formaldehyde. For example, the crude product stream may comprise at least 0.5 wt % alkylenating agent(s), e.g., at least 1 wt %, at least 5 wt %, at least 7 wt %, at least 10 wt %, or at least 25 wt %. In terms of ranges, the crude product stream may comprise from 0.5 wt % to 50 wt % alkylenating agent(s), e.g., from 1 wt % to 45 wt %, from 1 wt % to 25 wt %, from 1 wt % to 10 wt %, or from 5 wt % to 10 wt %. In terms of upper limits, the crude product stream may comprise at most 50 wt % alkylenating agent(s), e.g., at most 45 wt %, at most 25 wt %, or at most 10 wt %.

The crude acrylate product comprises at least 1 wt % acrylate product, e.g., at least 5 wt % or at least 10 wt %. In terms of ranges, the crude product stream may comprise from 1 wt % to 75 wt % acrylate product, e.g., from 1 wt % to 50 wt %, from 5 wt % to 50 wt %, or from 10 wt % to 40 wt %. In terms of upper limits, the crude product stream may comprise at most 75 wt % alkylenating agent(s), e.g., at most 50 wt %, or at most 40 wt %. Preferably the acrylate product is acrylic acid.

In one embodiment, the crude product stream of the present invention further comprises water. For example, the crude product stream may comprise less than 50 wt % water, e.g., less than 40 wt %, less than 30 wt %, or less than 25 wt %. In terms of ranges, the crude product stream may comprise from 1 wt % to 50 wt % water, e.g., from 5 wt % to 40 wt %, from 10 wt % to 30 wt %, or from 15 wt % to 25 wt %. In terms of upper limits, the crude product stream may comprise at least 1 wt % water, e.g., at least 5 wt %, at least 10 wt %, or at least 15 wt %.

In one embodiment, the crude product stream of the present invention comprises very little, if any, of the impurities found in most conventional acrylic acid crude product streams. For example, the crude product stream of the present invention may comprise less than 1000 wppm of such impurities (either as individual components or collectively), e.g., less than 500 wppm, less than 100 wppm, less than 50 wppm, or less than 10 wppm. Exemplary impurities include acetylene, ketene, beta-propiolactone, higher alcohols, e.g., $C_{2+}$, $C_{3+}$, or $C_{4+}$, and combinations thereof. Importantly, the crude product stream of the present invention comprises very little, if any, furfural and/or acrolein. In one embodiment, the crude product stream comprises substantially no furfural and/or acrolein, e.g., no furfural and/or acrolein. In one embodiment, the crude product stream comprises less than less than 500 wppm acrolein, e.g., less than 100 wppm, less than 50 wppm, or less than 10 wppm. In one embodiment, the crude product stream comprises less than less than 500 wppm furfural, e.g., less than 100 wppm, less than 50 wppm, or less than 10 wppm. Furfural and acrolein are known to act as detrimental chain terminators in acrylic acid polymerization reactions. Also, furfural and/or acrolein are known to have adverse effects on the color of purified product and/or to subsequent polymerized products.

In addition to the acrylic acid and the alkylenating agent, the crude product stream may further comprise acetic acid, water, propionic acid, and light ends such as oxygen, nitrogen, carbon monoxide, carbon dioxide, methanol, methyl acetate, methyl acrylate, acetaldehyde, hydrogen, and acetone. In one embodiment, because the exemplary oxygen amounts are employed, carbon monoxide and/or carbon dioxide production in inhibited. For example, the crude acrylate product may comprise less than 20 wt % carbon monoxide and/or carbon dioxide, e.g., less than 15 wt %, less than 10 wt % or less than 5 wt %. In one embodiment, a weight ratio of carbon monoxide and carbon dioxide, combined, to acrylate product is less than 0.50, e.g., less than 0.46, less than 0.4, or less than 0.25.

Exemplary compositional data for the crude product stream are shown in Table 1. The compositional data in Table 1 reflects the composition of the crude product stream that is fed to the separation zone if 1) nitrogen dilution conditions are not employed; or 2) nitrogen dilution conditions are employed and at least a major portion, preferably substantially all, of the nitrogen used in the nitrogen dilution is removed from the crude product stream before being fed to the separation zone. Components other than those listed in Table 1 may also be present in the crude product stream.

TABLE 1

| CRUDE ACRYLATE PRODUCT STREAM COMPOSITIONS | | | | |
|---|---|---|---|---|
| Component | Conc. (wt %) | Conc. (wt %) | Conc. (wt %) | Conc. (wt %) |
| Acrylic Acid | 1 to 75 | 1 to 50 | 5 to 50 | 10 to 40 |
| Alkylenating Agent(s) | 0.5 to 50 | 1 to 45 | 1 to 25 | 1 to 10 |
| Acetic Acid | 1 to 90 | 1 to 70 | 5 to 50 | 10 to 50 |
| Water | 1 to 50 | 5 to 40 | 10 to 30 | 15 to 25 |
| Propionic Acid | 0.01 to 10 | 0.1 to 10 | 0.1 to 5 | 0.1 to 1 |

TABLE 1-continued

CRUDE ACRYLATE PRODUCT STREAM COMPOSITIONS

| Component | Conc. (wt %) | Conc. (wt %) | Conc. (wt %) | Conc. (wt %) |
|---|---|---|---|---|
| Oxygen | 0.01 to 10 | 0.1 to 10 | 0.1 to 5 | 0.1 to 1 |
| Nitrogen | 0.1 to 20 | 0.1 to 10 | 0.5 to 5 | 0.5 to 4 |
| Carbon Monoxide | 0.01 to 10 | 0.1 to 10 | 0.1 to 5 | 0.5 to 3 |
| Carbon Dioxide | 0.01 to 10 | 0.1 to 10 | 0.1 to 5 | 0.5 to 3 |
| Other Light Ends | 0.01 to 10 | 0.1 to 10 | 0.1 to 5 | 0.5 to 3 |

Any suitable reaction and/or separation scheme may be employed to form the crude product stream as long as the reaction provides the crude product stream components that are discussed above. For example, in some embodiments, the acrylate product stream is formed by contacting an alkanoic acid, e.g., acetic acid, or an ester thereof with an alkylenating agent, e.g., a methylenating agent, for example formaldehyde, under conditions effective to form the crude acrylate product stream. Preferably, the contacting is performed over a suitable catalyst. The crude product stream may be the reaction product of the alkanoic acid-alkylenating agent reaction. In a preferred embodiment, the crude product stream is the reaction product of the aldol condensation reaction of acetic acid and formaldehyde, which is conducted over a catalyst comprising vanadium and titanium. In one embodiment, the crude product stream is the product of a reaction where methanol and acetic acid are combined to generate formaldehyde in situ. The aldol condensation then follows. In one embodiment, a methanol-formaldehyde solution is reacted with acetic acid to form the crude product stream.

The alkanoic acid, or an ester of the alkanoic acid, may be of the formula R'—CH$_2$—COOR, where R and R' are each, independently, hydrogen or a saturated or unsaturated alkyl or aryl group. As an example, R and R' may be a lower alkyl group containing for example 1-4 carbon atoms. In one embodiment, an alkanoic acid anhydride may be used as the source of the alkanoic acid. In one embodiment, the reaction is conducted in the presence of an alcohol, preferably the alcohol that corresponds to the desired ester, e.g., methanol. In addition to reactions used in the production of acrylic acid, the inventive catalyst, in other embodiments, may be employed to catalyze other reactions.

The alkanoic acid, e.g., acetic acid, may be derived from any suitable source including natural gas, petroleum, coal, biomass, and so forth. As examples, acetic acid may be produced via methanol carbonylation, acetaldehyde oxidation, ethylene oxidation, oxidative fermentation, and anaerobic fermentation.

As petroleum and natural gas prices fluctuate, becoming either more or less expensive, methods for producing acetic acid and intermediates such as methanol and carbon monoxide from alternate carbon sources have drawn increasing interest. In particular, when petroleum is relatively expensive compared to natural gas, it may become advantageous to produce acetic acid from synthesis gas ("syngas") that is derived from any available carbon source. U.S. Pat. No. 6,232,352, which is hereby incorporated by reference, for example, teaches a method of retrofitting a methanol plant for the manufacture of acetic acid. By retrofitting a methanol plant, the large capital costs associated with carbon monoxide generation for a new acetic acid plant are significantly reduced or largely eliminated. All or part of the syngas is diverted from the methanol synthesis loop and supplied to a separator unit to recover carbon monoxide and hydrogen, which are then used to produce acetic acid.

In some embodiments, at least some of the raw materials for the above-described aldol condensation process may be derived partially or entirely from syngas. For example, the acetic acid may be formed from methanol and carbon monoxide, both of which may be derived from syngas. For example, the methanol may be formed by steam reforming syngas, and the carbon monoxide may be separated from syngas. In other embodiments, the methanol may be formed in a carbon monoxide unit, e.g., as described in EP2076480; EP1923380; EP2072490; EP1914219; EP1904426; EP2072487; EO2072492; EP2072486; EP2060553; EP1741692; EP1907344; EP2060555; EP2186787; EP2072488; and U.S. Pat. No. 7,842,844, which are hereby incorporated by reference. Of course, this listing of methanol sources is merely exemplary and is not meant to be limiting. In addition, the above-identified methanol sources, inter alia, may be used to form the formaldehyde, e.g., in situ, which, in turn may be reacted with the acetic acid to form the acrylic acid. The syngas, in turn, may be derived from variety of carbon sources. The carbon source, for example, may be selected from the group consisting of natural gas, oil, petroleum, coal, biomass, and combinations thereof. Syngas or hydrogen may also be obtained from bio-derived methane gas, such as bio-derived methane gas produced by landfills or agricultural waste.

In another embodiment, in addition to the acetic acid formed via methanol carbonylation, some additional acetic acid may be formed from the fermentation of biomass and may be used in the hydrogenation step. The fermentation process preferably utilizes an acetogenic process or a homoacetogenic microorganism to ferment sugars to acetic acid producing little, if any, carbon dioxide as a by-product. The carbon efficiency for the fermentation process preferably is greater than 70%, greater than 80% or greater than 90% as compared to conventional yeast processing, which typically has a carbon efficiency of about 67%. Optionally, the microorganism employed in the fermentation process is of a genus selected from the group consisting of *Clostridium, Lactobacillus, Moorella, Thermoanaerobacter, Propionibacterium, Propionispera, Anaerobiospirillum*, and *Bacteriodes*, and in particular, species selected from the group consisting of *Clostridium formicoaceticum, Clostridium butyricum, Moorella thermoacetica, Thermoanaerobacter kivui, Lactobacillus delbrukii, Propionibacterium acidipropionici, Propionispera arboris, Anaerobiospirillum succinicproducens, Bacteriodes amylophilus* and *Bacteriodes ruminicola*. Optionally in this process, all or a portion of the unfermented residue from the biomass, e.g., lignans, may be gasified to form hydrogen that may be used in the hydrogenation step of the present invention. Exemplary fermentation processes for forming acetic acid are disclosed in U.S. Pat. Nos. 6,509,180; 6,927,048; 7,074,603; 7,507,562; 7,351,559; 7,601,865; 7,682,812; and 7,888,082, the entireties of which are incorporated herein by reference. See also U.S. Pub. Nos. 2008/0193989 and 2009/0281354, the entireties of which are incorporated herein by reference.

Examples of biomass include, but are not limited to, agricultural wastes, forest products, grasses, and other cellulosic material, timber harvesting residues, softwood chips, hardwood chips, tree branches, tree stumps, leaves, bark, sawdust, off-spec paper pulp, corn, corn stover, wheat straw, rice straw, sugarcane bagasse, switchgrass, miscanthus, animal manure, municipal garbage, municipal sewage, commercial waste, grape pumice, almond shells, pecan shells, coconut shells, coffee grounds, grass pellets, hay pellets, wood pellets, cardboard, paper, plastic, and cloth. See, e.g., U.S. Pat. No. 7,884, 253, the entirety of which is incorporated herein by reference. Another biomass source is black liquor, a thick, dark liquid that is a byproduct of the Kraft process for transforming wood into pulp, which is then dried to make paper. Black liquor is an aqueous solution of lignin residues, hemicellulose, and inorganic chemicals.

Methanol carbonylation processes suitable for production of acetic acid are described in U.S. Pat. Nos. 7,208,624, 7,115,772, 7,005,541, 6,657,078, 6,627,770, 6,143,930, 5,599,976, 5,144,068, 5,026,908, 5,001,259, and 4,994,608, all of which are hereby incorporated by reference.

U.S. Pat. No. RE 35,377, which is hereby incorporated by reference, provides a method for the production of methanol by conversion of carbonaceous materials such as oil, coal, natural gas and biomass materials. The process includes hydrogasification of solid and/or liquid carbonaceous materials to obtain a process gas which is steam pyrolized with additional natural gas to form syn gas. The syn gas is converted to methanol which may be carbonylated to acetic acid. U.S. Pat. No. 5,821,111, which discloses a process for converting waste biomass through gasification into syn gas, as well as U.S. Pat. No. 6,685,754 are hereby incorporated by reference.

In one optional embodiment, the acetic acid that is utilized in the condensation reaction comprises acetic acid and may also comprise other carboxylic acids, e.g., propionic acid, esters, and anhydrides, as well as acetaldehyde and acetone. In one embodiment, the acetic acid fed to the condensation reaction comprises propionic acid. For example, the acetic acid fed to the reaction may comprise from 0.001 wt % to 15 wt % propionic acid, e.g., from 0.001 wt % to 0.11 wt %, from 0.125 wt % to 12.5 wt %, from 1.25 wt % to 11.25 wt %, or from 3.75 wt % to 8.75 wt %. Thus, the acetic acid feed stream may be a cruder acetic acid feed stream, e.g., a less-refined acetic acid feed stream.

As used herein, "alkylenating agent" means an aldehyde or precursor to an aldehyde suitable for reacting with the alkanoic acid, e.g., acetic acid, to form an unsaturated acid, e.g., acrylic acid, or an alkyl acrylate. In preferred embodiments, the alkylenating agent comprises a methylenating agent such as formaldehyde, which preferably is capable of adding a methylene group ($=CH_2$) to the organic acid. Other alkylenating agents may include, for example, acetaldehyde, propanal, butanal, aryl aldehydes, benzyl aldehydes, alcohols, and combinations thereof. This listing is not exclusive and is not meant to limit the scope of the invention. In one embodiment, an alcohol may serve as a source of the alkylenating agent. For example, the alcohol may be reacted in situ to form the alkylenating agent, e.g., the aldehyde.

The alkylenating agent, e.g., formaldehyde, may be derived from any suitable source. Exemplary sources may include, for example, aqueous formaldehyde solutions, anhydrous formaldehyde derived from a formaldehyde drying procedure, trioxane, diether of methylene glycol, and paraformaldehyde. In a preferred embodiment, the formaldehyde is produced via a methanol oxidation process, which reacts methanol and oxygen to yield the formaldehyde.

In other embodiments, the alkylenating agent is a compound that is a source of formaldehyde. Where forms of formaldehyde that are not as freely or weakly complexed are used, the formaldehyde will form in situ in the condensation reactor or in a separate reactor prior to the condensation reactor. Thus for example, trioxane may be decomposed over an inert material or in an empty tube at temperatures over 350° C. or over an acid catalyst at over 100° C. to form the formaldehyde.

In one embodiment, the alkylenating agent corresponds to Formula I.

Formula I

In Formula I, $R_5$ and $R_6$ may be independently selected from $C_1$-$C_{12}$ hydrocarbons, preferably, $C_1$-$C_{12}$ alkyl, alkenyl or aryl, or hydrogen. Preferably, $R_5$ and $R_6$ are independently $C_1$-$C_6$ alkyl or hydrogen, with methyl and/or hydrogen being most preferred. X may be either oxygen or sulfur, preferably oxygen; and n is an integer from 1 to 10, preferably 1 to 3. In some embodiments, m is 1 or 2, preferably 1.

In one embodiment, the compound of formula I may be the product of an equilibrium reaction between formaldehyde and methanol in the presence of water. In such a case, the compound of formula I may be a suitable formaldehyde source. In one embodiment, the formaldehyde source includes any equilibrium composition. Examples of formaldehyde sources include but are not restricted to methylal (1,1 dimethoxymethane); polyoxymethylenes —$(CH_2—O)_i$— wherein i is from 1 to 100; formalin; and other equilibrium compositions such as a mixture of formaldehyde, methanol, and methyl propionate. In one embodiment, the source of formaldehyde is selected from the group consisting of 1,1 dimethoxymethane; higher formulas of formaldehyde and methanol; and $CH_3$—O—$(CH_2—O)_i$—$CH_3$ where i is 2.

The alkylenating agent may be used with or without an organic or inorganic solvent.

As discussed above, in some embodiments, the alkylenating agent that is reacted with the alkanoic acid may be provided to the process in the form of a crude alkylenating agent stream. The crude alkylenating agent stream comprises alkylenating agent, e.g., formaldehyde, and at least one other impurity, e.g., water and/or methanol. Preferably, the crude alkylenating agent stream comprises formalin. The term "formalin," refers to a mixture of formaldehyde, methanol, and water. In one embodiment, formalin comprises from 37 wt % to 55 wt % formaldehyde, from 44 wt % to 60 wt % water, and from 0.01 wt % to 25 wt % methanol. In cases where a mixture of formaldehyde, methanol, and methyl propionate is used, the mixture comprises less than 10 wt % water, e.g., less than 5 wt % or less than 1 wt %. In accordance with the present invention, the crude alkylenating agent may be dehydrated to reduce impurity content in the crude alkylenating agent stream, e.g., to remove water from the crude alkylenating agent stream.

In some embodiments, the condensation reaction may achieve favorable conversion of acetic acid and favorable selectivity and productivity to acrylates. For purposes of the present invention, the term "conversion" refers to the amount of acetic acid in the feed that is converted to a compound other than acetic acid. Conversion is expressed as a percentage based on acetic acid in the feed. The conversion of acetic acid may be at least 10%, e.g., at least 20%, at least 40%, or at least 50%.

Selectivity, as it refers to the formation of acrylate product, is expressed as the ratio of the amount of carbon in the desired product(s) and the amount of carbon in the total products. This ratio may be multiplied by 100 to arrive at the selectivity. Preferably, the catalyst selectivity to acrylate products, e.g., acrylic acid and methyl acrylate, is at least 40 mol %, e.g., at least 50 mol %, at least 60 mol %, or at least 70 mol %. In some embodiments, the selectivity to acrylic acid is at least 30 mol %, e.g., at least 40 mol %, or at least 50 mol %; and/or the selectivity to methyl acrylate is at least 10 mol %, e.g., at least 15 mol %, or at least 20 mol %.

The terms "productivity" or "space time yield" as used herein, refers to the grams of a specified product, e.g., acrylate products, formed per hour during the condensation based on the liters of catalyst used. A productivity of at least 20 grams of acrylate product per liter catalyst per hour, e.g., at least 100 grams of acrylates per liters catalyst per hour or at least 200 grams of acrylates per liter catalyst per hour, is preferred. In terms of ranges, the productivity preferably is from 20 to 1000 grams of acrylates per liter catalyst per hour, e.g., from 20 to 700 grams of acrylates per liter catalyst per hour or from 100 to 600 grams of acrylates per liter catalyst per hour or from 200 to 600 grams of acrylates per liter catalyst per hour or from 300 to 700 grams of acrylates per liter catalyst per hour.

In one embodiment, the inventive process yields at least 1,800 kg/hr of finished acrylic acid, e.g., at least 3,500 kg/hr, at least 18,000 kg/hr, or at least 37,000 kg/hr.

Formation of alkanes, e.g., ethane, may be low, and ideally less than 2%, less than 1%, or less than 0.5% of the acetic acid passed over the catalyst is converted to alkanes, which have little value other than as fuel.

The alkanoic acid or ester thereof and alkylenating agent may be fed independently or after prior mixing to a reactor containing the catalyst. The reactor may be any suitable reactor or combination of reactors. Preferably, the reactor comprises a fixed bed reactor or a series of fixed bed reactors. In one embodiment, the reactor is a packed bed reactor or a series of packed bed reactors. In one embodiment, the reactor is a fixed bed reactor. Of course, other reactors such as a continuous stirred tank reactor or a fluidized bed reactor, may be employed.

In some embodiments, the alkanoic acid, e.g., acetic acid, and the alkylenating agent, e.g., formaldehyde, are fed to the reactor at a molar ratio of at least 0.10:1, e.g., at least 0.75:1 or at least 1:1. In terms of ranges the molar ratio of alkanoic acid to alkylenating agent may range from 0.10:1 to 10:1 or from 0.75:1 to 5:1. In some embodiments, the reaction of the alkanoic acid and the alkylenating agent is conducted with a stoichiometric excess of alkanoic acid. In these instances, acrylate selectivity may be improved. As an example the acrylate selectivity may be at least 10% higher than a selectivity achieved when the reaction is conducted with an excess of alkylenating agent, e.g., at least 20% higher or at least 30% higher. In other embodiments, the reaction of the alkanoic acid and the alkylenating agent is conducted with a stoichiometric excess of alkylenating agent.

The condensation reaction may be conducted at a temperature of at least 250° C., e.g., at least 300° C., or at least 350° C. In terms of ranges, the reaction temperature may range from 200° C. to 500° C., e.g., from 250° C. to 400° C., or from 250° C. to 350° C. Residence time in the reactor may range from 1 second to 200 seconds, e.g., from 1 second to 100 seconds. Reaction pressure is not particularly limited, and the reaction is typically performed near atmospheric pressure. In one embodiment, the reaction may be conducted at a pressure ranging from 0 kPa to 4100 kPa, e.g., from 3 kPa to 345 kPa, or from 6 kPa to 103 kPa. The acetic acid conversion, in some embodiments, may vary depending upon the reaction temperature.

In one embodiment, the reaction is conducted at a gas hourly space velocity ("GHSV") greater than 600 $hr^{-1}$, e.g., greater than 1000 $hr^{-1}$ or greater than 2000 $hr^{-1}$. In one embodiment, the GHSV ranges from 600 $hr^{-1}$ to 10000 $hr^{-1}$, e.g., from 1000 $hr^{-1}$ to 8000 $hr^{-1}$ or from 1500 $hr^{-1}$ to 7500 $hr^{-1}$. As one particular example, when GHSV is at least 2000 $hr^{-1}$, the acrylate product STY may be at least 150 g/hr/liter.

In one embodiment, the unreacted components such as the alkanoic acid and formaldehyde as well as the inert or reactive gases that remain are recycled to the reactor after sufficient separation from the desired product.

When the desired product is an unsaturated ester made by reacting an ester of an alkanoic acid ester with formaldehyde, the alcohol corresponding to the ester may also be fed to the reactor either with or separately to the other components. For example, when methyl acrylate is desired, methanol may be fed to the reactor. The alcohol, amongst other effects, reduces the quantity of acids leaving the reactor. It is not necessary that the alcohol is added at the beginning of the reactor and it may for instance be added in the middle or near the back, in order to effect the conversion of acids such as propionic acid, methacrylic acid to their respective esters without depressing catalyst activity. In one embodiment, the alcohol may be added downstream of the reactor.

Catalyst Composition

The catalyst may be any suitable catalyst composition. As one example, condensation catalyst consisting of mixed oxides of vanadium and phosphorus have been investigated and described in M. Ai, *J. Catal.*, 107, 201 (1987); M. Ai, *J. Catal.*, 124, 293 (1990); M. Ai, *Appl. Catal.*, 36, 221 (1988); and M. Ai, *Shokubai*, 29, 522 (1987). Other examples include binary vanadium-titanium phosphates, vanadium-silica-phosphates, and alkali metal-promoted silicas, e.g., cesium- or potassium-promoted silicas.

In a preferred embodiment, the inventive process employs a catalyst composition comprising vanadium, titanium, and optionally at least one oxide additive. The oxide additive(s), if present, are preferably present in the active phase of the catalyst. In one embodiment, the oxide additive(s) are selected from the group consisting of silica, alumina, zirconia, and mixtures thereof or any other metal oxide other than metal oxides of titanium or vanadium. Preferably, the molar ratio of oxide additive to titanium in the active phase of the catalyst composition is greater than 0.05:1, e.g., greater than 0.1:1, greater than 0.5:1, or greater than 1:1. In terms of ranges, the molar ratio of oxide additive to titanium in the inventive catalyst may range from 0.05:1 to 20:1, e.g., from 0.1:1 to 10:1, or from 1:1 to 10:1. In these embodiments, the catalyst comprises titanium, vanadium, and one or more oxide additives and have relatively high molar ratios of oxide additive to titanium.

In other embodiments, the catalyst may further comprise other compounds or elements (metals and/or non-metals). For example, the catalyst may further comprise phosphorus and/or oxygen. In these cases, the catalyst may comprise from 15 wt % to 45 wt % phosphorus, e.g., from 20 wt % to 35 wt % or from 23 wt % to 27 wt %; and/or from 30 wt % to 75 wt % oxygen, e.g., from 35 wt % to 65 wt % or from 48 wt % to 51 wt %.

In some embodiments, the catalyst further comprises additional metals and/or oxide additives. These additional metals and/or oxide additives may function as promoters. If present, the additional metals and/or oxide additives may be selected from the group consisting of copper, molybdenum, tungsten, nickel, niobium, and combinations thereof. Other exemplary promoters that may be included in the catalyst of the invention include lithium, sodium, magnesium, aluminum, chromium, manganese, iron, cobalt, calcium, yttrium, ruthenium, silver, tin, barium, lanthanum, the rare earth metals, hafnium, tantalum, rhenium, thorium, bismuth, antimony, germanium, zirconium, uranium, cesium, zinc, and silicon and mixtures thereof. Other modifiers include boron, gallium, arsenic, sulfur, halides, Lewis acids such as $BF_3$, $ZnBr_2$, and $SnCl_4$. Exemplary processes for incorporating promoters into catalyst are described in U.S. Pat. No. 5,364,824, the entirety of which is incorporated herein by reference.

If the catalyst comprises additional metal(s) and/or metal oxides(s), the catalyst optionally may comprise additional metals and/or metal oxides in an amount from 0.001 wt % to 30 wt %, e.g., from 0.01 wt % to 5 wt % or from 0.1 wt % to 5 wt %. If present, the promoters may enable the catalyst to have a weight/weight space time yield of at least 25 grams of acrylic acid/gram catalyst-h, e.g., least 50 grams of acrylic acid/gram catalyst-h, or at least 100 grams of acrylic acid/gram catalyst-h.

In some embodiments, the catalyst is unsupported. In these cases, the catalyst may comprise a homogeneous mixture or a heterogeneous mixture as described above. In one embodiment, the homogeneous mixture is the product of an intimate mixture of vanadium and titanium oxides, hydroxides, and phosphates resulting from preparative methods such as controlled hydrolysis of metal alkoxides or metal complexes. In other embodiments, the heterogeneous mixture is the product of a physical mixture of the vanadium and titanium phosphates. These mixtures may include formulations prepared from phosphorylating a physical mixture of preformed hydrous metal oxides. In other cases, the mixture(s) may include a mixture of preformed vanadium pyrophosphate and titanium pyrophosphate powders.

In another embodiment, the catalyst is a supported catalyst comprising a catalyst support in addition to the vanadium, titanium, oxide additive, and optionally phosphorous and oxygen, in the amounts indicated above (wherein the molar ranges indicated are without regard to the moles of catalyst support, including any vanadium, titanium, oxide additive, phosphorous or oxygen contained in the catalyst support). The total weight of the support (or modified support), based on the total weight of the catalyst, preferably is from 75 wt % to 99.9 wt %, e.g., from 78 wt % to 97 wt %, or from 80 wt % to 95 wt %. The support may vary widely. In one embodiment, the support material is selected from the group consisting of silica, alumina, zirconia, titania, aluminosilicates, zeolitic materials, mixed metal oxides (including but not limited to binary oxides such as $SiO_2$—$Al_2O_3$, $SiO_2$—$TiO_2$, $SiO_2$—$ZnO$, $SiO_2$—$MgO$, $SiO_2$—$ZrO_2$, $Al_2O_3$—$MgO$, $Al_2O_3$—$TiO_2$, $Al_2O_3$—$ZnO$, $TiO_2$—$MgO$, $TiO_2$—$ZrO_2$, $TiO_2$—$ZnO$, $TiO_2$—$SnO_2$) and mixtures thereof, with silica being one preferred support. In embodiments where the catalyst comprises a titania support, the titania support may comprise a major or minor amount of rutile and/or anatase titanium dioxide. Other suitable support materials may include, for example, stable metal oxide-based supports or ceramic-based supports. Preferred supports include silicaceous supports, such as silica, silica/alumina, a Group IIA silicate such as calcium metasilicate, pyrogenic silica, high purity silica, silicon carbide, sheet silicates or clay minerals such as montmorillonite, beidellite, saponite, pillared clays, other microporous and mesoporous materials, and mixtures thereof. Other supports may include, but are not limited to, iron oxide, magnesia, steatite, magnesium oxide, carbon, graphite, high surface area graphitized carbon, activated carbons, and mixtures thereof. These listings of supports are merely exemplary and are not meant to limit the scope of the present invention.

In some embodiments, a zeolitic support is employed. For example, the zeolitic support may be selected from the group consisting of montmorillonite, $NH_4$ ferrierite, H-mordenite-PVOx, vermiculite-1, H-ZSMS, NaY, H-SDUSY, Y zeolite with high SAR, activated bentonite, H-USY, MONT-2, HY, mordenite SAR 20, SAPO-34, Aluminosilicate (X), VUSY, Aluminosilicate (CaX), Re-Y, and mixtures thereof. H-SDUSY, VUSY, and H-USY are modified Y zeolites belonging to the faujasite family. In one embodiment, the support is a zeolite that does not contain any metal oxide modifier(s). In some embodiments, the catalyst composition comprises a zeolitic support and the active phase comprises a metal selected from the group consisting of vanadium, aluminum, nickel, molybdenum, cobalt, iron, tungsten, zinc, copper, titanium cesium bismuth, sodium, calcium, chromium, cadmium, zirconium, and mixtures thereof. In some of these embodiments, the active phase may also comprise hydrogen, oxygen, and/or phosphorus.

In other embodiments, in addition to the active phase and a support, the inventive catalyst may further comprise a support modifier. A modified support, in one embodiment, relates to a support that includes a support material and a support modifier, which, for example, may adjust the chemical or physical properties of the support material such as the acidity or basicity of the support material. In embodiments that use a modified support, the support modifier is present in an amount from 0.1 wt % to 50 wt %, e.g., from 0.2 wt % to 25 wt %, from 0.5 wt % to 15 wt %, or from 1 wt % to 8 wt %, based on the total weight of the catalyst composition.

In one embodiment, the support modifier is an acidic support modifier. In some embodiments, the catalyst support is modified with an acidic support modifier. The support modifier similarly may be an acidic modifier that has a low volatility or little volatility. The acidic modifiers may be selected from the group consisting of oxides of Group IVB metals, oxides of Group VB metals, oxides of Group VIB metals, iron oxides, aluminum oxides, and mixtures thereof. In one embodiment, the acidic modifier may be selected from the group consisting of $WO_3$, $MoO_3$, $Fe_2O_3$, $Cr_2O_3$, $V_2O_5$, $MnO_2$, $CuO$, $Co_2O_3$, $Bi_2O_3$, $TiO_2$, $ZrO_2$, $Nb_2O_5$, $Ta_2O_5$, $Al_2O_3$, $B_2O_3$, $P_2O_5$, and $Sb_2O_3$.

In another embodiment, the support modifier is a basic support modifier. The presence of chemical species such as alkali and alkaline earth metals, are normally considered basic and may conventionally be considered detrimental to catalyst performance. The presence of these species, however, surprisingly and unexpectedly, may be beneficial to the catalyst performance. In some embodiments, these species may act as catalyst promoters or a necessary part of the acidic catalyst structure such in layered or sheet silicates such as montmorillonite. Without being bound by theory, it is postulated that these cations create a strong dipole with species that create acidity.

Additional modifiers that may be included in the catalyst include, for example, boron, aluminum, magnesium, zirconium, and hafnium.

As will be appreciated by those of ordinary skill in the art, the support materials, if included in the catalyst of the present invention, preferably are selected such that the catalyst system is suitably active, selective and robust under the process conditions employed for the formation of the desired product, e.g., acrylic acid or alkyl acrylate. Also, the active metals and/or pyrophosphates that are included in the catalyst of the invention may be dispersed throughout the support, coated on the outer surface of the support (egg shell) or decorated on the surface of the support. In some embodiments, in the case of macro- and meso-porous materials, the active sites may be anchored or applied to the surfaces of the pores that are distributed throughout the particle and hence are surface sites available to the reactants but are distributed throughout the support particle.

The inventive catalyst may further comprise other additives, examples of which may include: molding assistants for enhancing moldability; reinforcements for enhancing the strength of the catalyst; pore-forming or pore modification agents for formation of appropriate pores in the catalyst, and binders. Examples of these other additives include stearic acid, graphite, starch, cellulose, silica, alumina, glass fibers, silicon carbide, and silicon nitride. Preferably, these additives do not have detrimental effects on the catalytic performances, e.g., conversion and/or activity. These various additives may be added in such an amount that the physical strength of the catalyst does not readily deteriorate to such an extent that it becomes impossible to use the catalyst practically as an industrial catalyst.

Separation

The unique crude product of the present invention may be separated in a separation zone to form a final product, e.g., a (purified) final acrylic acid product. The inventive process comprises the step of separating at least a portion of the crude product to form at least one alkylenating agent stream and at least one purified acrylate product stream.

There has been little if any disclosure relating to separation schemes that may be employed to effectively purify the unique crude product that is produced. Other conventional reactions, e.g., propylene oxidation or ketene/formaldehyde, do not yield crude products that comprises higher amounts of formaldehyde. The primary reactions and the side reactions in propylene oxidation do not create formaldehyde. In the reaction of ketene and formaldehyde, a two-step reaction is employed and the formaldehyde is confined to the first stage. Also, the ketene is highly reactive and converts substantially all of the reactant formaldehyde. As a result of these features, very little, if any, formaldehyde remains in the crude product exiting the reaction zone. Because no formaldehyde is present in crude products formed by these conventional reactions, the separation schemes associated therewith have not addressed the problems and unpredictability that accompany crude products that have higher formaldehyde content.

In one embodiment, the separation comprises the step of separating at least a portion of the crude product stream to form an alkylenating agent stream and an intermediate product stream. This separating step may be referred to as an "alkylenating agent split." In one embodiment, the alkylenating agent stream comprises significant amounts of alkylenating agent(s). For example, the alkylenating agent stream may comprise at least 1 wt % alkylenating agent(s), e.g., at least 5 wt %, at least 10 wt %, at least 15 wt %, or at least 25 wt %. In terms of ranges, the alkylenating stream may comprise from 1 wt % to 75 wt % alkylenating agent(s), e.g., from 3 wt % to 50 wt %, from 3 wt % to 25 wt %, or from 10 wt % to 20 wt %. In terms of upper limits, the alkylenating stream may comprise less than 75 wt % alkylenating agent(s), e.g. less than 50 wt % or less than 40 wt %. In preferred embodiments, the alkylenating agent is formaldehyde.

As noted above, the presence of alkylenating agent in the crude product stream adds unpredictability and problems to separation schemes. Without being bound by theory, it is believed that formaldehyde reacts in many side reactions with water to form by-products. The following side reactions are exemplary.

Without being bound by theory, it is believed that, in some embodiments, as a result of these reactions, the alkylenating agent, e.g., formaldehyde, acts as a "light" component at higher temperatures and as a "heavy" component at lower temperatures. The reaction(s) are exothermic. Accordingly, the equilibrium constant increases as temperature decreases and decreases as temperature increases. At lower temperatures, the larger equilibrium constant favors methylene glycol and oligomer production and formaldehyde becomes limited, and, as such, behaves as a heavy component. At higher temperatures, the smaller equilibrium constant favors formaldehyde production and methylene glycol becomes limited. As such, formaldehyde behaves as a light component. In view of these difficulties, as well as others, the separation of streams that comprise water and formaldehyde cannot be expected to behave as a typical two-component system. These features contribute to the unpredictability and difficulty of the separation of the unique crude product stream of the present invention.

The present invention, surprisingly and unexpectedly, achieves effective separation of alkylenating agent(s) from the inventive crude product stream to yield a purified product comprising acrylate product and very low amounts of other impurities.

In one embodiment, the alkylenating split is performed such that a lower amount of acetic acid is present in the resulting alkylenating stream. Preferably, the alkylenating agent stream comprises little or no acetic acid. As an example, the alkylenating agent stream, in some embodiments, comprises less than 50 wt % acetic acid, e.g., less than 45 wt %, less than 25 wt %, less than 10 wt %, less than 5 wt %, less than 3 wt %, or less than 1 wt %. Surprisingly and unexpectedly, the present invention provides for the lower amounts of acetic acid in the alkylenating agent stream, which, beneficially reduces or eliminates the need for further treatment of the alkylenating agent stream to remove acetic acid. In some embodiments, the alkylenating agent stream may be treated to remove water therefrom, e.g., to purge water.

In some embodiments, the alkylenating agent split is performed in at least one column, e.g., at least two columns or at least three columns. Preferably, the alkylenating agent is performed in a two column system. In other embodiments, the alkylenating agent split is performed via contact with an extraction agent. In other embodiments, the alkylenating agent split is performed via precipitation methods, e.g., crystallization, and/or azeotropic distillation. Of course, other suitable separation methods may be employed either alone or in combination with the methods mentioned herein.

The intermediate product stream comprises acrylate products. In one embodiment, the intermediate product stream comprises a significant portion of acrylate products, e.g., acrylic acid. For example, the intermediate product stream may comprise at least 5 wt % acrylate products, e.g., at least 25 wt %, at least 40 wt %, at least 50 wt %, or at least 60 wt %. In terms of ranges, the intermediate product stream may comprise from 5 wt % to 99 wt % acrylate products, e.g. from 10 wt % to 90 wt %, from 25 wt % to 75 wt %, or from 35 wt % to 65 wt %. The intermediate product stream, in one embodiment, comprises little if any alkylenating agent. For example, the intermediate product stream may comprise less than 1 wt % alkylenating agent, e.g., less than 0.1 wt %, less than 0.05 wt %, or less than 0.01 wt %. In addition to the acrylate products, the intermediate product stream optionally comprises acetic acid, water, propionic acid and other components.

In some cases, the intermediate acrylate product stream comprises higher amounts of alkylenating agent. For example, in one embodiment, the intermediate acrylate product stream comprises from 1 wt % to 50 wt % alkylenating agent, e.g., from 1 wt % to 10 wt % or from 5 wt % to 50 wt %. In terms of limits, the intermediate acrylate product stream may comprise at least 1 wt % alkylenating agent, e.g., at least 5 wt % or at least 10 wt %.

In one embodiment, the crude product stream is optionally treated, e.g. separated, prior to the separation of alkylenating agent therefrom. In such cases, the treatment(s) occur before the alkylenating agent split is performed. In other embodiments, at least a portion of the intermediate acrylate product stream may be further treated after the alkylenating agent split. As one example, the crude product stream may be treated to remove light ends therefrom. This treatment may occur either before or after the alkylenating agent split, preferably before the alkylenating agent split. In some of these cases, the further treatment of the intermediate acrylate product stream may result in derivative streams that may be considered to be additional purified acrylate product streams. In other embodiments, the further treatment of the intermediate acrylate product stream results in at least one finished acrylate product stream.

In one embodiment, the inventive process operates at a high process efficiency. For example, the process efficiency may be at least 10%, e.g., at least 20% or at least 35%. In one embodiment, the process efficiency is calculated based on the flows of reactants into the reaction zone. The process efficiency may be calculated by the following formula.

$$\text{Process Efficiency} = 2N_{HAcA}/[N_{HOAc} + N_{HCHO} + N_{H2O}]$$

where:

$N_{HAeA}$ is the molar production rate of acrylate products; and $N_{HOAc}$, $N_{HCHO}$, and $N_{H2O}$ are the molar feed rates of acetic acid, formaldehyde, and water.

Figure 1:
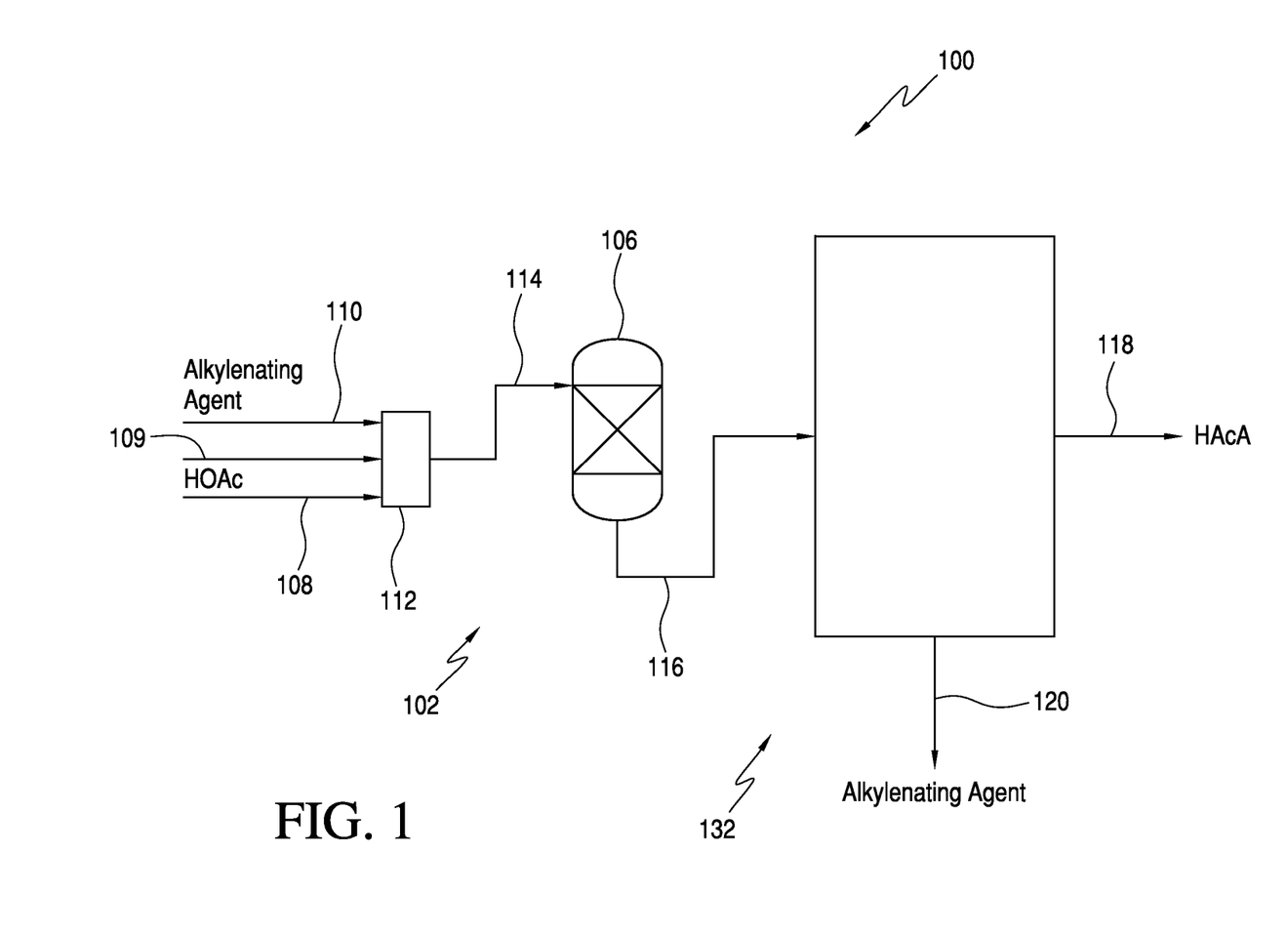
FIG. 1 is a process flowsheet showing an acrylic acid reaction/separation system in accordance with an embodiment of the present invention.

As discussed above, the crude product stream is separated to yield an intermediate acrylate product stream. FIG. 1 is a flow diagram depicting the formation of the crude product stream and the separation thereof to obtain an intermediate acrylate product stream. Acrylate product system 100 comprises reaction zone 102 and alkylenating agent split zone 132. Reaction zone 102 comprises reactor 106, alkanoic acid feed, e.g., acetic acid feed, 108, oxygen feed 109, alkylenating agent feed, e.g., formaldehyde feed 110, and vaporizer 112.

Acetic acid, oxygen, and formaldehyde are fed to vaporizer 112 via lines 108, 109, and 110, respectively, to create a vapor feed stream, which exits vaporizer 112 via line 114 and is directed to reactor 106. In one embodiment, the vapor stream is considered a reaction mixture, as discussed herein, containing the inventive amounts of oxygen. In one embodiment, lines 108, 109, and 110 may be combined and jointly fed to the vaporizer 112. The temperature of the vapor feed stream in line 114 is preferably from 200° C. to 600° C., e.g., from 250° C. to 500° C. or from 340° C. to 425° C. Alternatively, a vaporizer may not be employed and one or more of the reactants may be fed directly to reactor 106.

Any feed that is not vaporized may be removed from vaporizer 112 and may be recycled or discarded. In addition, although line 114 is shown as being directed to the upper half of reactor 106, line 114 may be directed to the middle or bottom of first reactor 106. Further modifications and additional components to reaction zone 102 and alkylenating agent split zone 132 are described below.

Reactor 106 contains the catalyst that is used in the reaction to form crude product stream, which is withdrawn, preferably continuously, from reactor 106 via line 116. Although FIG. 1 shows the crude product stream being withdrawn from the bottom of reactor 106, the crude product stream may be withdrawn from any portion of reactor 106. Exemplary composition ranges for the crude product stream are shown in Table 1 above.

In one embodiment, one or more guard beds (not shown) may be used upstream of the reactor to protect the catalyst from poisons or undesirable impurities contained in the feed or return/recycle streams. Such guard beds may be employed in the vapor or liquid streams. Suitable guard bed materials may include, for example, carbon, silica, alumina, ceramic, or resins. In one aspect, the guard bed media is functionalized, e.g., silver functionalized, to trap particular species such as sulfur or halogens.

Figure 2:
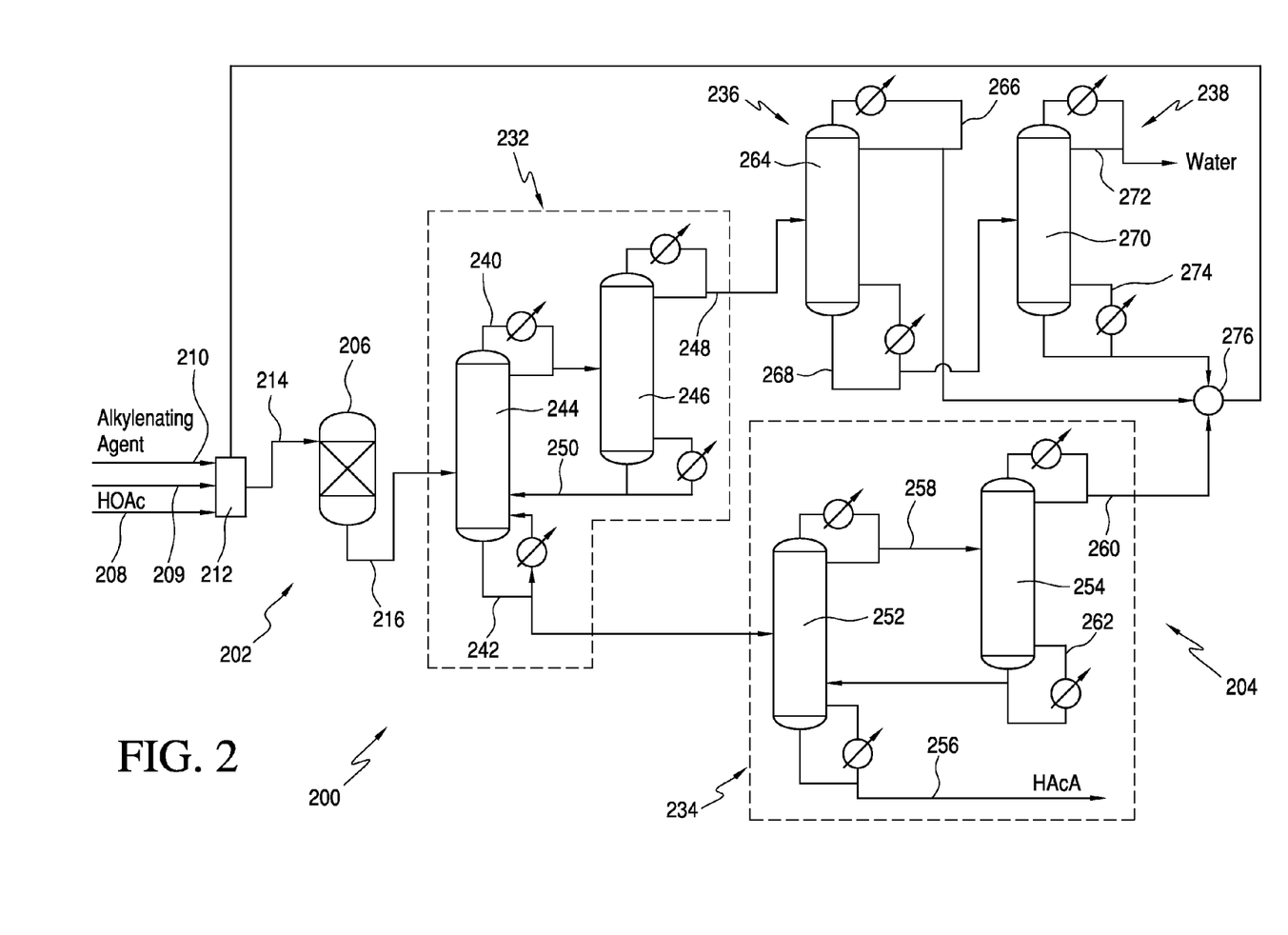
FIG. 2 is a schematic diagram of an acrylic acid reaction/separation system in accordance with one embodiment of the present invention.
Figure 3:
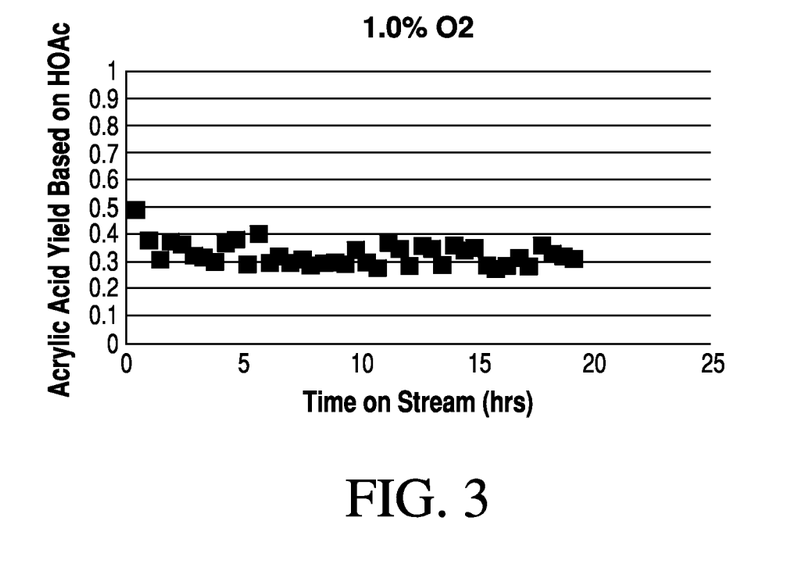
FIG. 3 is a graph showing the reaction yields over time achieved by a process in accordance with one embodiment of the present invention.
Figure 4:
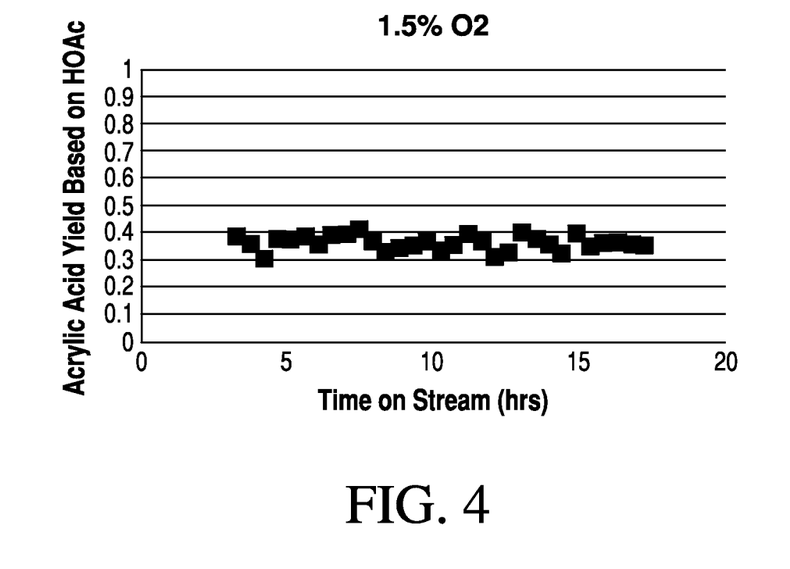
FIG. 4 is a graph showing the reaction yields over time achieved by a process in accordance with one embodiment of the present invention.
Figure 5:
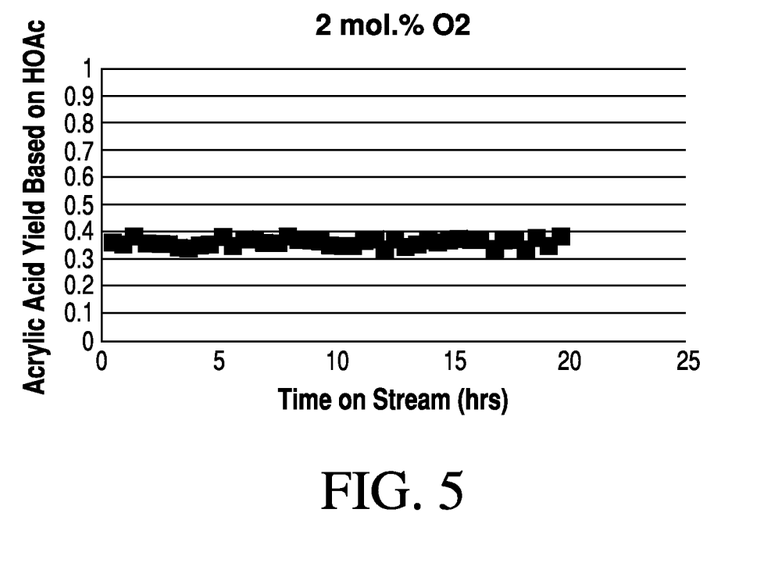
FIG. 5 is a graph showing the reaction yields over time achieved by a process in accordance with one embodiment of the present invention.
Figure 6:
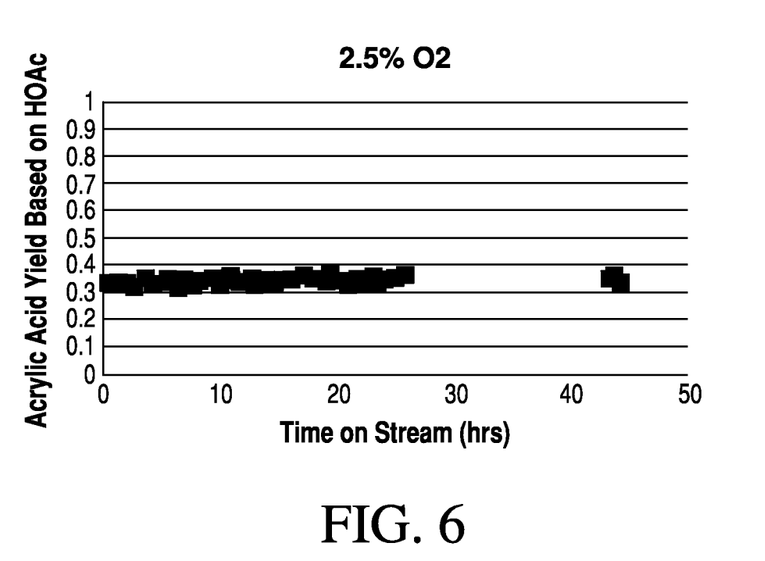
FIG. 6 is a graph showing the reaction yields over time achieved by a process in accordance with one embodiment of the present invention.
Figure 7:
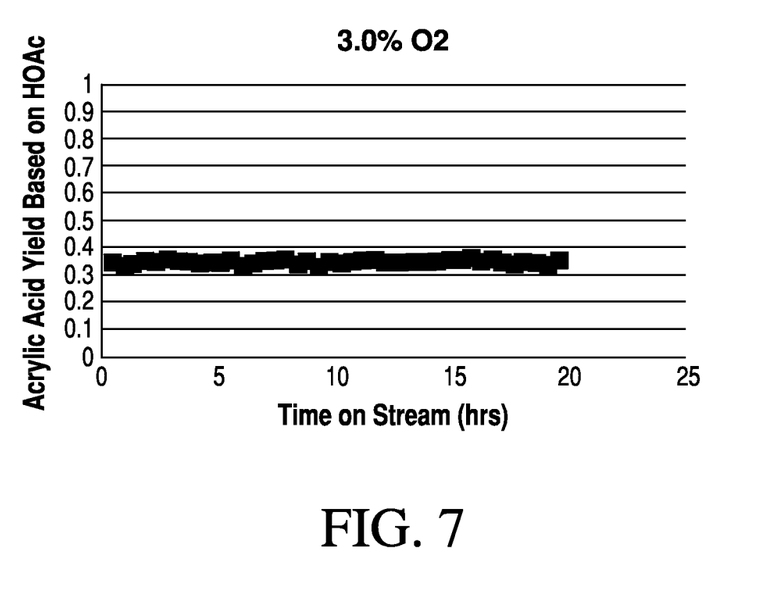
FIG. 7 is a graph showing the reaction yields over time achieved by a process in accordance with one embodiment of the present invention.

The crude product stream in line 116 is fed to alkylenating agent split unit 132. Alkylenating agent split unit 132 may comprise one or more separation units, e.g., two or more or three or more. In one example, the alkylenating agent split unit contains multiple columns, as shown in FIG. 2. Alkylenating agent split unit 132 separates the crude product stream into at least one intermediate acrylate product stream, which exits via line 118 and at least one alkylenating agent stream, which exits via line 120. Exemplary compositional ranges for the intermediate acrylate product stream are shown in Table 2. Components other than those listed in Table 2 may also be present in the intermediate acrylate product stream. Examples include methanol, methyl acetate, methyl acrylate, dimethyl ketone, carbon dioxide, carbon monoxide, oxygen, nitrogen, and acetone.

TABLE 2

INTERMEDIATE ACRYLATE PRODUCT STREAM COMPOSITION

| | Conc. (wt %) | Conc. (wt %) | Conc. (wt %) |
|---|---|---|---|
| Acrylic Acid | at least 5 | 5 to 99 | 35 to 65 |
| Acetic Acid | less than 95 | 5 to 90 | 20 to 60 |
| Water | less than 25 | 0.1 to 10 | 0.5 to 7 |
| Alkylenating Agent | <1 | <0.5 | <0.1 |
| Propionic Acid | <10 | 0.01 to 5 | 0.01 to 1 |

In other embodiments, the intermediate acrylate product stream comprises higher amounts of alkylenating agent. For example, the intermediate acrylate product stream may comprise from 1 wt % to 10 wt % alkylenating agent, e.g., from 1 wt % to 8 wt % or from 2 wt % to 5 wt %. In one embodiment, the intermediate acrylate product stream comprises greater than 1 wt % alkylenating agent, e.g., greater than 5 wt % or greater than 10 wt %.

Exemplary compositional ranges for the alkylenating agent stream are shown in Table 3. Components other than those listed in Table 3 may also be present in the purified alkylate product stream. Examples include methanol, methyl acetate, methyl acrylate, dimethyl ketone, carbon dioxide, carbon monoxide, nitrogen, and acetone.

TABLE 3

ALKYLENATING AGENT STREAM COMPOSITION

| | Conc. (wt %) | Conc. (wt %) | Conc. (wt %) |
|---|---|---|---|
| Acrylic Acid | less than 15 | 0.01 to 10 | 0.1 to 5 |
| Acetic Acid | 10 to 65 | 20 to 65 | 25 to 55 |
| Water | 15 to 75 | 25 to 65 | 30 to 60 |
| Alkylenating Agent | at least 1 | 1 to 75 | 10 to 20 |
| Propionic Acid | <10 | 0.001 to 5 | 0.001 to 1 |

In other embodiments, the alkylenating stream comprises lower amounts of acetic acid. For example, the alkylenating agent stream may comprise less than 10 wt % acetic acid, e.g., less than 5 wt % or less than 1 wt %.

As mentioned above, the crude product stream of the present invention comprises little, if any, furfural and/or acrolein. As such the derivative stream(s) of the crude product streams will comprise little, if any, furfural and/or acrolein. In one embodiment, the derivative stream(s), e.g., the streams of the separation zone, comprises less than 500 wppm acrolein, e.g., less than 100 wppm, less than 50 wppm, or less than 10 wppm. In one embodiment, the derivative stream(s)

comprises less than less than 500 wppm furfural, e.g., less than 100 wppm, less than 50 wppm, or less than 10 wppm.

FIG. 2 shows an overview of a reaction/separation scheme in accordance with the present invention. Acrylate product system 200 comprises reaction zone 202 and separation zone 204. Reaction zone 202 comprises reactor 206, alkanoic acid feed, e.g., acetic acid feed, 208, oxygen feed 209, alkylenating agent feed, e.g., formaldehyde feed, 210, vaporizer 212, and line 214. Reaction zone 202 and the components thereof function in a manner similar to reaction zone 102 of FIG. 1.

Reaction zone 202 yields a crude product stream, which exits reaction zone 202 via line 216 and is directed to separation zone 204. The components of the crude product stream are discussed above. Separation zone 204 comprises alkylenating agent split unit 232, acrylate product split unit 234, acetic acid split unit 236, and drying unit 238. Separation zone 204 may also comprise an optional light ends removal unit (not shown). For example, the light ends removal unit may comprise a condenser and/or a flasher. The light ends removal unit may be configured either upstream or downstream of the alkylenating agent split unit. Depending on the configuration, the light ends removal unit removes light ends from the crude product stream, the alkylenating stream, and/or the intermediate acrylate product stream. In one embodiment, when the light ends are removed, the remaining liquid phase comprises the acrylic acid, acetic acid, alkylenating agent, and/or water.

Alkylenating agent split unit 232 may comprise any suitable separation device or combination of separation devices. For example, alkylenating agent split unit 232 may comprise a column, e.g., a standard distillation column, an extractive distillation column and/or an azeotropic distillation column. In other embodiments, alkylenating agent split unit 232 comprises a precipitation unit, e.g., a crystallizer and/or a chiller. Preferably, alkylenating agent split unit 232 comprises two standard distillation columns. In another embodiment, the alkylenating agent split is performed by contacting the crude product stream with a solvent that is immiscible with water. For example alkylenating agent split unit 232 may comprise at least one liquid-liquid extraction columns. In another embodiment, the alkylenating agent split is performed via azeotropic distillation, which employs an azeotropic agent. In these cases, the azeotropic agent may be selected from the group consisting of methyl isobutylketene, o-xylene, toluene, benzene, n-hexane, cyclohexane, p-xylene, and mixtures thereof. This listing is not exclusive and is not meant to limit the scope of the invention. In another embodiment, the alkylenating agent split is performed via a combination of distillation, e.g., standard distillation, and crystallization. Of course, other suitable separation devices may be employed either alone or in combination with the devices mentioned herein.

In FIG. 2, alkylenating agent split unit 232 comprises first column 244 and second column 246. Alkylenating agent split unit 232 receives crude acrylic product stream in line 216 and separates same into at least one alkylenating agent stream, e.g., stream 248, and at least one purified product stream, e.g., stream 242. Alkylenating agent split unit 232 performs an alkylenating agent split, as discussed above.

In operation, as shown in FIG. 2, the crude product stream in line 216 is directed to first column 244. First column 244 separates the crude product stream a distillate in line 240 and a residue in line 242. The distillate may be refluxed and the residue may be boiled up as shown. Stream 240 comprises at least 1 wt % alkylenating agent. As such, stream 240 may be considered an alkylenating agent stream. The first column residue exits first column 244 in line 242 and comprises a significant portion of acrylate product. As such, stream 242 is an intermediate product stream. Exemplary compositional ranges for the distillate and residue of first column 244 are shown in Table 4. Components other than those listed in Table 4 may also be present in the residue and distillate.

TABLE 4

FIRST COLUMN

|  | Conc. (wt. %) | Conc. (wt. %) | Conc. (wt. %) |
|---|---|---|---|
| Distillate |  |  |  |
| Acrylic Acid | 0.1 to 20 | 1 to 10 | 1 to 5 |
| Acetic Acid | 25 to 65 | 35 to 55 | 40 to 50 |
| Water | 15 to 55 | 25 to 45 | 30 to 40 |
| Alkylenating Agent | at least 1 | 1 to 75 | 10 to 20 |
| Propionic Acid | <10 | 0.001 to 5 | 0.001 to 1 |
| Residue |  |  |  |
| Acrylic Acid | at least 5 | 5 to 99 | 35 to 65 |
| Acetic Acid | less than 95 | 5 to 90 | 20 to 60 |
| Water | less than 25 | 0.1 to 10 | 0.5 to 7 |
| Alkylenating Agent | <1 | <0.5 | <0.1 |
| Propionic Acid | <10 | 0.01 to 5 | 0.01 to 1 |

In one embodiments, the first distillate comprises smaller amounts of acetic acid, e.g., less than 25 wt %, less than 10 wt %, e.g., less than 5 wt % or less than 1 wt %. In one embodiment, the first residue comprises larger amounts of alkylenating agent, e.g., In other embodiments, the intermediate acrylate product stream comprises higher amounts of alkylenating agent, e.g., greater than 1 wt % greater than 5 wt % or greater than 10 wt %.

For convenience, the distillate and residue of the first column may also be referred to as the "first distillate" or "first residue." The distillates or residues of the other columns may also be referred to with similar numeric modifiers (second, third, etc.) in order to distinguish them from one another, but such modifiers should not be construed as requiring any particular separation order.

In one embodiment, polymerization inhibitors and/or anti-foam agents may be employed in the separation zone, e.g., in the units of the separation zone. The inhibitors may be used to reduce the potential for fouling caused by polymerization of acrylates. The anti-foam agents may be used to reduce potential for foaming in the various streams of the separation zone. The polymerization inhibitors and/or the anti-foam agents may be used at one or more locations in the separation zone.

Returning to FIG. 2, at least a portion of stream 240 is directed to second column 246. Second column 246 separates the at least a portion of stream 240 into a distillate in line 248 and a residue in line 250. The distillate may be refluxed and the residue may be boiled up as shown. The distillate comprises at least 1 wt % alkylenating agent. Stream 248, like stream 240, may be considered an alkylenating agent stream. The second column residue exits second column 246 in line 250 and comprises a significant portion of acetic acid. At least a portion of line 250 may be returned to first column 244 for further separation. In one embodiment, at least a portion of line 250 is returned, either directly or indirectly, to reactor 206. Exemplary compositional ranges for the distillate and residue of second column 246 are shown in Table 5. Components other than those listed in Table 5 may also be present in the residue and distillate.

TABLE 5

SECOND COLUMN

|  | Conc. (wt. %) | Conc. (wt. %) | Conc. (wt. %) |
|---|---|---|---|
| Distillate |  |  |  |
| Acrylic Acid | 0.01 to 10 | 0.05 to 5 | 0.1 to 0.5 |
| Acetic Acid | 10 to 50 | 20 to 40 | 25 to 35 |
| Water | 35 to 75 | 45 to 65 | 50 to 60 |
| Alkylenating Agent | at least 1 | 1 to 75 | 10 to 20 |
| Propionic Acid | 0.01 to 10 | 0.01 to 5 | 0.01 to 0.05 |
| Residue |  |  |  |
| Acrylic Acid | 0.1 to 25 | 0.05 to 15 | 1 to 10 |
| Acetic Acid | 40 to 80 | 50 to 70 | 55 to 65 |
| Water | 1 to 40 | 5 to 35 | 10 to 30 |
| Alkylenating Agent | at least 1 | 1 to 75 | 10 to 20 |
| Propionic Acid | <10 | 0.001 to 5 | 0.001 to 1 |

In cases where any of the alkylenating agent split unit comprises at least one column, the column(s) may be operated at suitable temperatures and pressures. In one embodiment, the temperature of the residue exiting the column(s) ranges from 90° C. to 130° C., e.g., from 95° C. to 120° C. or from 100° C. to 115° C. The temperature of the distillate exiting the column(s) preferably ranges from 60° C. to 90° C., e.g., from 65° C. to 85° C. or from 70° C. to 80° C. The pressure at which the column(s) are operated may range from 1 kPa to 300 kPa, e.g., from 10 kPa to 100 kPa or from 40 kPa to 80 kPa. In preferred embodiments, the pressure at which the column(s) are operated is kept at a low level e.g., less than 100 kPa, less than 80 kPa, or less than 60 kPa. In terms of lower limits, the column(s) may be operated at a pressures of at least 1 kPa, e.g., at least 20 kPa or at least 40 kPa. Without being bound by theory, it is believed that alkylenating agents, e.g., formaldehyde, may not be sufficiently volatile at lower pressures. Thus, maintenance of the column pressures at these levels surprisingly and unexpectedly provides for efficient separation operations. In addition, it has surprisingly and unexpectedly been found that be maintaining a low pressure in the columns of alkylenating agent split unit 232 may inhibit and/or eliminate polymerization of the acrylate products, e.g., acrylic acid, which may contribute to fouling of the column(s).

In one embodiment, the alkylenating agent split is achieved via one or more liquid-liquid extraction units. Preferably, the one or more liquid-liquid extraction units employ one or more extraction agents. Multiple liquid-liquid extraction units may be employed to achieve the alkylenating agent split. Any suitable liquid-liquid extraction devices used for multiple equilibrium stage separations may be used. Also, other separation devices, e.g., traditional columns, may be employed in conjunction with the liquid-liquid extraction unit(s).

In one embodiment (not shown), the crude product stream is fed to a liquid-liquid extraction column where the crude product stream is contacted with an extraction agent, e.g., an organic solvent. The liquid-liquid extraction column extracts the acids, e.g., acrylic acid and acetic acid, from the crude product stream. An aqueous stage comprising water, alkylenating agent, and some acetic acid exits the liquid-liquid extraction unit. Small amounts of acylic acid may also be present in the aqueous stream. The aqueous phase may be further treated and/or recycled. An organic phase comprising acrylic acid, acetic acid, and the extraction agent also exits the liquid-liquid extraction unit. The organic phase may also comprise water and formaldehyde. The acrylic acid may be separated from the organic phase and collected as product. The acetic acid may be separated then recycled and/or used elsewhere. The solvent may be recovered and recycled to the liquid-liquid extreaction unit.

The inventive process further comprises the step of separating the intermediate acrylate product stream to form a finished acrylate product stream and a first finished acetic acid stream. The finished acrylate product stream comprises acrylate product(s) and the first finished acetic acid stream comprises acetic acid. The separation of the acrylate products from the intermediate product stream to form the finished acrylate product may be referred to as the "acrylate product split."

Returning to FIG. 2, purified product stream 242 exits alkylenating agent split unit 232 and is directed to acrylate product split unit 234 for further separation, e.g., to further separate the acrylate products therefrom. Acrylate product split unit 234 may comprise any suitable separation device or combination of separation devices. For example, acrylate product split unit 234 may comprise at least one column, e.g., a standard distillation column, an extractive distillation column and/or an azeotropic distillation column. In other embodiments, acrylate product split unit 234 comprises a precipitation unit, e.g., a crystallizer and/or a chiller. Preferably, acrylate product split unit 234 comprises two standard distillation columns as shown in FIG. 2. In another embodiment, acrylate product split unit 234 comprises a liquid-liquid extraction unit. Of course, other suitable separation devices may be employed either alone or in combination with the devices mentioned herein.

In FIG. 2, acrylate product split unit 234 comprises third column 252 and fourth column 254. Acrylate product split unit 234 receives at least a portion of purified acrylic product stream in line 242 and separates same into finished acrylate product stream 256 and at least one acetic acid-containing stream. As such, acrylate product split unit 234 may yield the finished acrylate product.

As shown in FIG. 2, at least a portion of purified acrylic product stream in line 242 is directed to third column 252. Third column 252 separates the purified acrylic product stream to form third distillate, e.g., line 258, and third residue, which is the finished acrylate product stream, e.g., line 256. The distillate may be refluxed and the residue may be boiled up as shown.

Stream 258 comprises acetic acid and some acrylic acid. The third column residue exits third column 252 in line 256 and comprises a significant portion of acrylate product. As such, stream 256 is a finished product stream. Exemplary compositional ranges for the distillate and residue of third column 252 are shown in Table 6. Components other than those listed in Table 6 may also be present in the residue and distillate.

TABLE 6

THIRD COLUMN

|  | Conc. (wt. %) | Conc. (wt. %) | Conc. (wt. %) |
|---|---|---|---|
| Distillate |  |  |  |
| Acrylic Acid | 0.1 to 40 | 1 to 30 | 5 to 30 |
| Acetic Acid | 60 to 99 | 70 to 90 | 75 to 85 |
| Water | 0.1 to 25 | 0.1 to 10 | 1 to 5 |
| Alkylenating Agent | less than 1 | 0.001 to 1 | 0.1 to 1 |
| Propionic Acid | <10 | 0.001 to 5 | 0.001 to 1 |
| Residue |  |  |  |
| Acrylic Acid | at least 85 | 85 to 99.9 | 95 to 99.5 |
| Acetic Acid | less than 15 | 0.1 to 10 | 0.1 to 5 |

TABLE 6-continued

THIRD COLUMN

|  | Conc. (wt. %) | Conc. (wt. %) | Conc. (wt. %) |
|---|---|---|---|
| Water | less than 1 | less than 0.1 | less than 0.01 |
| Alkylenating Agent | less than 1 | 0.001 to 1 | 0.1 to 1 |
| Propionic Acid | 0.1 to 10 | 0.1 to 5 | 0.5 to 3 |

Returning to FIG. 2, at least a portion of stream 258 is directed to fourth column 254. Fourth column 254 separates the at least a portion of stream 258 into a distillate in line 260 and a residue in line 262. The distillate may be refluxed and the residue may be boiled up as shown. The distillate comprises a major portion of acetic acid. In one embodiment, at least a portion of line 260 is returned, either directly or indirectly, to reactor 206. The fourth column residue exits fourth column 254 in line 262 and comprises acetic acid and some acrylic acid. At least a portion of line 262 may be returned to third column 252 for further separation. In one embodiment, at least a portion of line 262 is returned, either directly or indirectly, to reactor 206. In another embodiment, at least a portion of the acetic acid-containing stream in either or both of lines 260 and 262 may be directed to an ethanol production system that utilizes the hydrogenation of acetic acid form the ethanol. In another embodiment, at least a portion of the acetic acid-containing stream in either or both of lines 260 and 262 may be directed to a vinyl acetate system that utilizes the reaction of ethylene, acetic acid, and oxygen form the vinyl acetate. Exemplary compositional ranges for the distillate and residue of fourth column 254 are shown in Table 7. Components other than those listed in Table 7 may also be present in the residue and distillate.

TABLE 7

FOURTH COLUMN

|  | Conc. (wt. %) | Conc. (wt. %) | Conc. (wt. %) |
|---|---|---|---|
| Distillate |  |  |  |
| Acrylic Acid | 0.01 to 10 | 0.05 to 5 | 0.1 to 1 |
| Acetic Acid | 50 to 99.9 | 70 to 99.5 | 80 to 99 |
| Water | 0.1 to 25 | 0.1 to 15 | 1 to 10 |
| Alkylenating Agent | less than 10 | 0.001 to 5 | 0.01 to 5 |
| Propionic Acid | 0.0001 to 10 | 0.001 to 5 | 0.001 to 0.05 |
| Residue |  |  |  |
| Acrylic Acid | 5 to 50 | 15 to 40 | 20 to 35 |
| Acetic Acid | 50 to 95 | 60 to 80 | 65 to 75 |
| Water | 0.01 to 10 | 0.01 to 5 | 0.1 to 1 |
| Alkylenating Agent | less than 1 | 0.001 to 1 | 0.1 to 1 |
| Propionic Acid | <10 | 0.001 to 5 | 0.001 to 1 |

In cases where the acrylate product split unit comprises at least one column, the column(s) may be operated at suitable temperatures and pressures. In one embodiment, the temperature of the residue exiting the column(s) ranges from 90° C. to 130° C., e.g., from 95° C. to 120° C. or from 100° C. to 115° C. The temperature of the distillate exiting the column(s) preferably ranges from 60° C. to 90° C., e.g., from 65° C. to 85° C. or from 70° C. to 80° C. The pressure at which the column(s) are operated may range from 1 kPa to 300 kPa, e.g., from 10 kPa to 100 kPa or from 40 kPa to 80 kPa. In preferred embodiments, the pressure at which the column(s) are operated is kept at a low level e.g., less than 50 kPa, less than 27 kPa, or less than 20 kPa. In terms of lower limits, the column(s) may be operated at a pressures of at least 1 kPa, e.g., at least 3 kPa or at least 5 kPa. Without being bound by theory, it has surprisingly and unexpectedly been found that be maintaining a low pressure in the columns of acrylate product split unit 234 may inhibit and/or eliminate polymerization of the acrylate products, e.g., acrylic acid, which may contribute to fouling of the column(s).

It has also been found that, surprisingly and unexpectedly, maintaining the temperature of acrylic acid-containing streams fed to acrylate product split unit 234 at temperatures below 140° C., e.g., below 130° C. or below 115° C., may inhibit and/or eliminate polymerization of acrylate products. In one embodiment, to maintain the liquid temperature at these temperatures, the pressure of the column(s) is maintained at or below the pressures mentioned above. In these cases, due to the lower pressures, the number of theoretical column trays is kept at a low level, e.g., less than 10, less than 8, less than 7, or less than 5. As such, it has surprisingly and unexpectedly been found that multiple columns having fewer trays inhibit and/or eliminate acrylate product polymerization. In contrast, a column having a higher amount of trays, e.g., more than 10 trays or more than 15 trays, would suffer from fouling due to the polymerization of the acrylate products. Thus, in a preferred embodiment, the acrylic acid split is performed in at least two, e.g., at least three, columns, each of which have less than 10 trays, e.g. less than 7 trays. These columns each may operate at the lower pressures discussed above.

The inventive process further comprises the step of separating an alkylenating agent stream to form a purified alkylenating stream and a purified acetic acid stream. The purified alkylenating agent stream comprises a significant portion of alkylenating agent, and the purified acetic acid stream comprises acetic acid and water. The separation of the alkylenating agent from the acetic acid may be referred to as the "acetic acid split."

Returning to FIG. 2, alkylenating agent stream 248 exits alkylenating agent split unit 232 and is directed to acetic acid split unit 236 for further separation, e.g., to further separate the alkylenating agent and the acetic acid therefrom. Acetic acid split unit 236 may comprise any suitable separation device or combination of separation devices. For example, acetic acid split unit 236 may comprise at least one column, e.g., a standard distillation column, an extractive distillation column and/or an azeotropic distillation column. In other embodiments, acetic acid split unit 236 comprises a precipitation unit, e.g., a crystallizer and/or a chiller. Preferably, acetic acid split unit 236 comprises a standard distillation column as shown in FIG. 2. In another embodiment, acetic acid split unit 236 comprises a liquid-liquid extraction unit. Of course, other suitable separation devices may be employed either alone or in combination with the devices mentioned herein.

In FIG. 2, acetic acid split unit 236 comprises fifth column 264. Acetic acid split unit 236 receives at least a portion of alkylenating agent stream in line 248 and separates same into a fifth distillate comprising alkylenating agent in line 266, e.g., a purified alkylenating stream, and a fifth residue comprising acetic acid in line 268, e.g., a purified acetic acid stream. The distillate may be refluxed and the residue may be boiled up as shown. In one embodiment, at least a portion of line 266 and/or line 268 are returned, either directly or indirectly, to reactor 206. At least a portion of stream in line 268 may be further separated. In another embodiment, at least a portion of the acetic acid-containing stream in line 268 may be directed to an ethanol production system that utilizes the hydrogenation of acetic acid form the ethanol. In another embodiment, at least a portion of the acetic acid-containing stream in either or both of lines 260 and 262 may be directed to a vinyl acetate system that utilizes the reaction of ethylene, acetic acid, and oxygen form the vinyl acetate.

The stream in line 266 comprises alkylenating agent and water. The stream in line 268 comprises acetic acid and water. Exemplary compositional ranges for the distillate and residue of fifth column 264 are shown in Table 8. Components other than those listed in Table 8 may also be present in the residue and distillate.

TABLE 8

FIFTH COLUMN

|  | Conc. (wt. %) | Conc. (wt. %) | Conc. (wt. %) |
|---|---|---|---|
| Distillate |  |  |  |
| Acrylic Acid | less than 1 | 0.001 to 5 | 0.001 to 1 |
| Acetic Acid | less than 1 | 0.001 to 5 | 0.001 to 1 |
| Water | 40 to 80 | 50 to 70 | 55 to 65 |
| Alkylenating Agent | 20 to 60 | 30 to 50 | 35 to 45 |
| Propionic Acid | less than 1 | 0.001 to 5 | 0.001 to 1 |
| Residue |  |  |  |
| Acrylic Acid | less than 1 | 0.01 to 5 | 0.1 to 1 |
| Acetic Acid | 25 to 65 | 35 to 55 | 40 to 50 |
| Water | 35 to 75 | 45 to 65 | 50 to 60 |
| Alkylenating Agent | less than 1 | 0.01 to 5 | 0.1 to 1 |
| Propionic Acid | less than 1 | 0.001 to 5 | 0.001 to 1 |

In cases where the acetic acid split unit comprises at least one column, the column(s) may be operated at suitable temperatures and pressures. In one embodiment, the temperature of the residue exiting the column(s) ranges from 90° C. to 130° C., e.g., from 95° C. to 120° C. or from 100° C. to 115° C. The temperature of the distillate exiting the column(s) preferably ranges from 60° C. to 90° C., e.g., from 65° C. to 85° C. or from 70° C. to 80° C. The pressure at which the column(s) are operated may range from 1 kPa to 500 kPa, e.g., from 25 kPa to 400 kPa or from 100 kPa to 300 kPa.

The inventive process further comprises the step of separating the purified acetic acid stream to form a second finished acetic acid stream and a water stream. The second finished acetic acid stream comprises a major portion of acetic acid, and the water stream comprises mostly water. The separation of the acetic acid from the water may be referred to as dehydration.

Returning to FIG. 2, fifth residue 268 exits acetic acid split unit 236 and is directed to drying unit 238 for further separation, e.g., to remove water from the acetic acid. Drying unit 238 may comprise any suitable separation device or combination of separation devices. For example, drying unit 238 may comprise at least one column, e.g., a standard distillation column, an extractive distillation column and/or an azeotropic distillation column. In other embodiments, drying unit 238 comprises a dryer and/or a molecular sieve unit. In a preferred embodiment, drying unit 238 comprises a liquid-liquid extraction unit. In one embodiment, drying unit 238 comprises a standard distillation column as shown in FIG. 2. Of course, other suitable separation devices may be employed either alone or in combination with the devices mentioned herein.

In FIG. 2, drying unit 238 comprises sixth column 270. Drying unit 238 receives at least a portion of second finished acetic acid stream in line 268 and separates same into a sixth distillate comprising a major portion of water in line 272 and a sixth residue comprising acetic acid and small amounts of water in line 274. The distillate may be refluxed and the residue may be boiled up as shown. In one embodiment, at least a portion of line 274 is returned, either directly or indirectly, to reactor 206. In another embodiment, at least a portion of the acetic acid-containing stream in line 274 may be directed to an ethanol production system that utilizes the hydrogenation of acetic acid form the ethanol. In another embodiment, at least a portion of the acetic acid-containing stream in either or both of lines 260 and 262 may be directed to a vinyl acetate system that utilizes the reaction of ethylene, acetic acid, and oxygen form the vinyl acetate.

Exemplary compositional ranges for the distillate and residue of sixth column 270 are shown in Table 9. Components other than those listed in Table 9 may also be present in the residue and distillate.

TABLE 9

SIXTH COLUMN

|  | Conc. (wt. %) | Conc. (wt. %) | Conc. (wt. %) |
|---|---|---|---|
| Distillate |  |  |  |
| Acrylic Acid | less than 1 | 0.001 to 5 | 0.001 to 1 |
| Acetic Acid | less than 1 | 0.01 to 5 | 0.01 to 1 |
| Water | 90 to 99.9 | 95 to 99.9 | 95 to 99.5 |
| Alkylenating Agent | less than 1 | 0.01 to 5 | 0.01 to 1 |
| Propionic Acid | less than 1 | 0.001 to 5 | 0.001 to 1 |
| Residue |  |  |  |
| Acrylic Acid | less than 1 | 0.01 to 5 | 0.01 to 1 |
| Acetic Acid | 75 to 99.9 | 85 to 99.5 | 90 to 99.5 |
| Water | 25 to 65 | 35 to 55 | 40 to 50 |
| Alkylenating Agent | less than 1 | less than 0.001 | less than 0.0001 |
| Propionic Acid | less than 1 | 0.001 to 5 | 0.001 to 1 |

In cases where the drying unit comprises at least one column, the column(s) may be operated at suitable temperatures and pressures. In one embodiment, the temperature of the residue exiting the column(s) ranges from 90° C. to 130° C., e.g., from 95° C. to 120° C. or from 100° C. to 115° C. The temperature of the distillate exiting the column(s) preferably ranges from 60° C. to 90° C., e.g., from 65° C. to 85° C. or from 70° C. to 80° C. The pressure at which the column(s) are operated may range from 1 kPa to 500 kPa, e.g., from 25 kPa to 400 kPa or from 100 kPa to 300 kPa. FIG. 2 also shows tank 276, which, collects at least one of the process streams prior to recycling same to reactor 206. Tank 276 is an optional feature. The various recycle streams that may, alternatively, be recycled directly to reactor 206 without being collected in tank 276.

EXAMPLES

Reaction mixtures comprising formaldehyde, oxygen, acetic acid, water, and nitrogen were reacted over a catalyst comprising vanadium and titanium in accordance with the present invention. The molar ratio of acetic acid to formaldehyde was approximately 1.5:1. The gas hourly space velocity was 2400 $hr^{-1}$. The reaction temperature was 370° C. For the various samples, concentrations of the formaldehyde, acetic acid, water, and nitrogen were maintained at essentially the same level. The concentration of oxygen was set at 1.0 wt %, 1.5 wt %, 2.0 wt %, 2.5 wt %, and 3.0 wt %. The acrylic acid yields were measured at various time periods.

FIGS. 3-7 are graphs showing the reaction yields over time of acrylic acid for samples using inventive concentrations of oxygen in the reaction mixture. As shown, when the inventive oxygen concentrations were employed, catalyst stability (as reflected in the reaction yield achieved) was consistent over the 20 hour time period and differences in reaction yield over time were reduced, as compared to the examples that employed oxygen concentrations outside of the inventive range.

Table 10 shows the effect of oxygen concentration on catalyst stability at various time periods. Catalyst performance is indicated by the yield that the reaction achieves. As shown, for the inventive process, the catalyst performance was consistent over extended periods of time. In contrast, when low amounts or no oxygen were utilized, catalyst performance drops 50% after only approximately two hours.

TABLE 10

REACTION YIELD OVER TIME, %

| Oxygen in Reaction Mixture, wt % | 1 minute (initial) | 5 Hours | 10 Hours | 15 Hours | 20 Hours |
|---|---|---|---|---|---|
| 1 wt % | 38.5 | 29.2 | 30.0 | 28.5 | 30.4 |
| 1.5 wt % | — | 37.5 | 36.4 | 39.0 | 35.0 |
| 2.0 wt % | 35.9 | 38.0 | 35.0 | 36.2 | 38.1 |
| 2.5 wt % | 33.9 | 33.5 | 32.8 | 33.4 | 34.1 |
| 3 wt % | 34.6 | 35.0 | 34.3 | 35.9 | 34.7 |
| Comparative | 15 min. | 52 min. | 91 mins. | 126 mins. | |
| No Oxygen | 40 | 32 | 25 | 20 | |

Also, in addition to the improvements in stability, the average yields over the 20 hour period for the inventive samples were 32.2, 36.0, 36.1, 34.2, and 34.5, respectively, which demonstrate significant unexpected improvements over conventional processes, e.g., where low amounts or no oxygen is employed. As shown in Table 10, the comparative example demonstrated an average yield of 29.2 over approximately a two hour period.

While the invention has been described in detail, modifications within the spirit and scope of the invention will be readily apparent to those of skill in the art. In view of the foregoing discussion, relevant knowledge in the art and references discussed above in connection with the Background and Detailed Description, the disclosures of which are all incorporated herein by reference. In addition, it should be understood that aspects of the invention and portions of various embodiments and various features recited below and/or in the appended claims may be combined or interchanged either in whole or in part. In the foregoing descriptions of the various embodiments, those embodiments which refer to another embodiment may be appropriately combined with other embodiments as will be appreciated by one of skill in the art. Furthermore, those of ordinary skill in the art will appreciate that the foregoing description is by way of example only, and is not intended to limit the invention.

We claim:

1. A process for producing an acrylate product, the process comprising the steps of:
    (a) reacting a reaction mixture comprising from 1 wt % to 40 wt % alkanoic acid, from 0.5 wt % to 35 wt % alkylenating agent, from 1 wt % to 60 wt % water, from 22 wt % to 97.5 wt % nitrogen, and from 1 wt % to 3 wt % oxygen over a catalyst and under conditions effective to form a crude acrylate product comprising acrylate product and alkylenating agent; and
    (b) separating at least a portion of the crude product to form at least one alkylenating agent stream and at least one purified acrylate product stream comprising acrylate product;
    wherein the reaction yield varies by less than 50% over the lifetime of the catalyst.

2. The process of claim 1, wherein the reaction mixture comprises from 1 wt % to 2 wt % oxygen.

3. The process of claim 1, wherein the reaction yield decreases by less than 5% after a predetermined period of time.

4. The process of claim 3, wherein the predetermined period of time is at least 1 hour.

5. The process of claim 1, wherein the reaction yield is greater than 20%.

6. The process of claim 1, wherein the molar ratio of acetic acid to oxygen ranges from 2:1 to 30:1.

7. The process of claim 1, wherein the selectivity to acrylate product is greater than 40%.

8. The process of claim 1, wherein the selectivity to carbon monoxide and carbon dioxide, combined, is less than 29%.

9. The process of claim 1, wherein the crude acrylate product comprises greater than 1 wt % acrylate product.

10. The process of claim 1, wherein the crude acrylate product comprises less than 20 wt % carbon monoxide and carbon dioxide.

11. The process of claim 1, wherein the weight ratio of carbon monoxide and carbon dioxide, combined, to acrylate product in the crude acrylate product is less than 0.50.

12. The process of claim 1, wherein the reaction mixture further comprises water and nitrogen.

13. The process of claim 12, wherein the reaction mixture comprises:
    at least 74 wt % nitrogen.

14. The process of claim 1, wherein the catalyst comprises vanadium, titanium, bismuth, tungsten, or mixtures thereof.

15. A process for producing an acrylate product, the process comprising the steps of:
    (a) reacting a reaction mixture comprising an alkanoic acid, alkylenating agent, and oxygen over a catalyst comprising at least one metal selected from the group consisting of titanium, and at least one of vanadium, bismuth and tungsten and under conditions effective to form a crude acrylate product comprising acrylate product and alkylenating agent; and
    (b) separating at least a portion of the crude product to form at least one alkylenating agent stream and at least one purified acrylate product stream comprising acrylate product;
    wherein the reaction mixture comprises from 1 wt. % to 3 wt. % oxygen; and
    wherein the reaction yield varies by less than 50% over the lifetime of the catalyst.

* * * * *